(12) United States Patent
Akui et al.

(10) Patent No.: US 7,959,561 B2
(45) Date of Patent: Jun. 14, 2011

(54) ENDOSCOPE SYSTEM HAVING RIGID ENDOSCOPE AND WIPER SHEATH

(75) Inventors: Nobuaki Akui, Hino (JP); Kazuo Banju, Hachioji (JP); Takumi Dejima, Mitaka (JP)

(73) Assignee: Olympus Medical Systems Corp., Tokyo (JP)

( * ) Notice: Subject to any disclaimer, the term of this patent is extended or adjusted under 35 U.S.C. 154(b) by 1491 days.

(21) Appl. No.: 11/353,521

(22) Filed: Feb. 14, 2006

(65) Prior Publication Data

US 2006/0199998 A1 Sep. 7, 2006

(30) Foreign Application Priority Data

Feb. 14, 2005 (JP) ................................. 2005-036978

(51) Int. Cl.
*A61B 1/12* (2006.01)
*A61B 1/00* (2006.01)
(52) U.S. Cl. .................. 600/157; 600/158; 600/121
(58) Field of Classification Search .................. 600/127, 600/104, 106, 107, 114, 131, 146, 121–125, 600/153–159; 15/32
See application file for complete search history.

(56) References Cited

U.S. PATENT DOCUMENTS

| | | | | |
|---|---|---|---|---|
| 5,313,934 A * | 5/1994 | Wiita et al. | ............ | 600/109 |
| 5,392,766 A | 2/1995 | Masterson | | |
| 5,518,502 A * | 5/1996 | Kaplan et al. | ............ | 600/157 |
| 5,830,126 A * | 11/1998 | Odanaka et al. | ............ | 600/156 |
| 6,126,592 A * | 10/2000 | Proch et al. | ............ | 600/114 |
| 2003/0139649 A1* | 7/2003 | Kasahara et al. | ............ | 600/157 |
| 2004/0267090 A1* | 12/2004 | Ueno et al. | ............ | 600/106 |

FOREIGN PATENT DOCUMENTS

| | | |
|---|---|---|
| JP | 4-362912 | 12/1992 |
| JP | 6-189893 | 7/1994 |
| JP | 8-29699 | 2/1996 |
| JP | 2002-224014 | 8/2002 |
| JP | 2003-199703 | 7/2003 |
| JP | 2003-310628 | 11/2003 |

* cited by examiner

*Primary Examiner* — Thomas J Sweet
*Assistant Examiner* — Ryan Henderson
(74) *Attorney, Agent, or Firm* — Scully, Scott, Murphy & Presser, P.C.

(57) ABSTRACT

An endoscope system includes a rigid endoscope including an optical system in a rigid insert section thereof, and a wiper sheath. The wiper sheath includes a wiper insert section receiving the insert section of the rigid endoscope, a wiper arranged on a distal end portion of the wiper insert section and enabled to be placed in contact with a distal-end face of the rigid endoscope received in the wiper insert section, and an operation unit, arranged at a proximal end portion of the wiper insert section, for switching the wiper between a contact state with the wiper placed to be in contact with the distal-end face of the rigid endoscope and a detached state with the wiper spaced apart from the distal-end face of the rigid endoscope, and for moving the wiper on and along the distal-end face of the rigid endoscope when the wiper is in the contact state.

8 Claims, 18 Drawing Sheets

ENDOSCOPE SYSTEM HAVING RIGID ENDOSCOPE AND WIPER SHEATH

This application claims benefit of Japanese Application No. 2005-36978 filed on Feb. 14, 2005, the contents of which are incorporated by this reference.

BACKGROUND OF THE INVENTION

1. Field of the Invention

The present invention relates to an endoscope system for wiping off water and a body fluid stuck on a distal-end face of a rigid endoscope with a wiper.

2. Description of the Related Art

Endoscope systems, such as rigid endoscopes, are widely used in surgical operations. During such a surgical operation, a body fluid, blood, etc. may stick to the distal-end face of each rigid endoscope, more particularly, an observation window, thereby degrading observation performance of the endoscope. To achieve sufficient observation performance, the observation window needs to be sufficiently cleaned.

As a cleaning method of cleaning the observation window, a body fluid, blood, etc. may be removed by pushing and pulling the rigid endoscope. However, this method inconveniences a physician.

For example, in the endoscope disclosed in Japanese Unexamined Patent Application Publication No. 6-189893, cleaning means cleans the distal end of an insert section of the endoscope by feeding water to the distal-end face through a nozzle of a water feed channel from a water passage.

An image scope, disclosed in Japanese Unexamined Patent Application Publication No. 8-29699, employs a nozzle to eject washing liquid, and a wiper to wipe contaminated water, contaminant matter, and body fluids sticking to an observation window of the image scope.

The image scope, mainly used for maintenance of a sewage pipe system, does not take cleaning and disinfection operations into consideration. There is a need for an endoscope system that is easy to use and allows the distal-end face thereof to be well cleaned.

SUMMARY OF THE INVENTION

An endoscope system of the present invention includes a rigid endoscope including an observation optical system and an illumination optical system in a rigid insert section thereof, and a wiper sheath. The sheath includes a wiper insert section receiving the insert section of the rigid endoscope, a wiper arranged on a distal end of the wiper insert section and enabled to be placed in contact with a distal-end face of the rigid endoscope received in the wiper insert section, and an operation unit, arranged at a proximal end portion of the wiper insert section, for switching the wiper between a contact state with the wiper placed to be in contact with the distal-end face of the rigid endoscope and a detached state with the wiper spaced apart from the distal-end face of the rigid endoscope, and for moving the wiper on and along the distal-end face of the rigid endoscope when the wiper is in the contact state.

The above and other objects, features and advantages of the invention will become more clearly understood from the following description referring to the accompanying drawings.

DETAILED DESCRIPTION OF THE PREFERRED EMBODIMENTS

The embodiment of the present invention is described below with reference to the drawings.

The preferred embodiment of the present invention is described below with reference to FIGS. 1 through 24.

Figure 1:
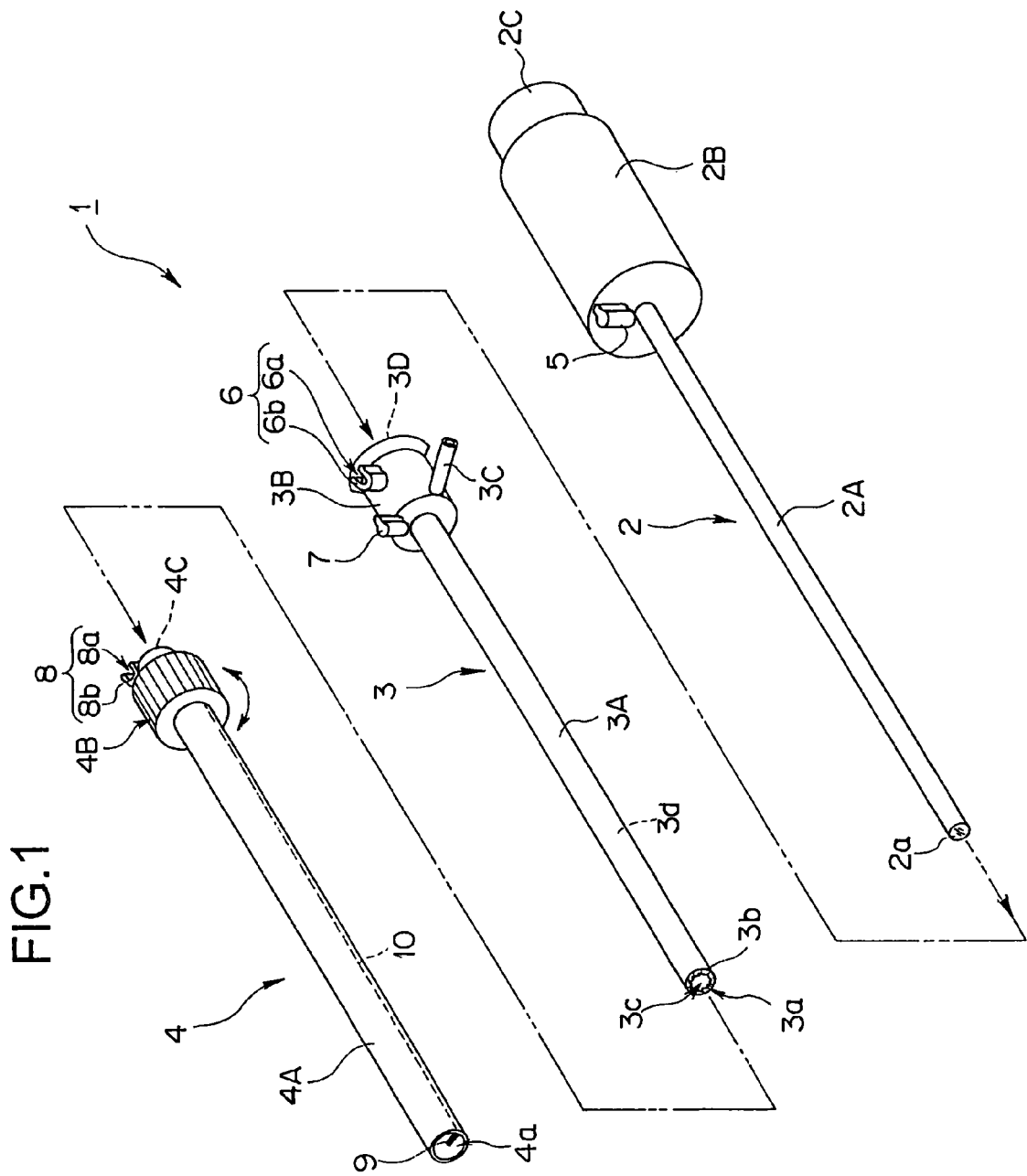
FIG. 1 is an exploded perspective view illustrating a structure of an endoscope system of the present invention.

As shown in FIG. 1, an endoscope system 1 includes a rigid endoscope 2 having a rigid insert section 2A, a washing sheath 3, and a wiper sheath 4. An observation optical system and an illumination optical system are arranged toward a distal-end face 2a of the rigid insert section 2A from inside. The rigid insert section 2A of the rigid endoscope 2 is inserted through a sheath insert section 3A of the washing sheath 3. The sheath insert section 3A of the washing sheath 3 is inserted through a wiper insert section 4A of a wiper sheath 4.

The rigid endoscope 2 includes the insert section 2A, a grip section 2B, and an eyepiece section 2C. The rigid insert section 2A is inserted into a body cavity of a subject. The grip section 2B is arranged on the proximal end of the insert section 2A. The eyepiece section 2C is arranged on the proximal end of the grip section 2B.

The illumination optical system and the observation optical system are arranged within the insert section 2A. The illumination optical system illuminates a region within an abdominal cavity of the subject. The observation optical system captures an observation image of the region within the abdominal cavity illuminated by the illumination optical system. The grip section 2B is provided with a light-guide connector (not shown).

The light-guide connector (not shown) connects to a connector arranged at one end of a light-guide cable. The other end of the light-guide cable connects to a light-source device. Illumination light from the light-source device is guided to the region within the abdominal cavity via the light-guide cable and the illumination optical system and illuminates the abdominal region.

A camera head (not shown) containing a charge-coupled device (CCD) is able to be connected to the eyepiece section 2C. The observation image of the region within the abdominal cavity is captured by the CCD in the camera head through the observation optical system. An electrical signal responsive to the observation image captured by the CCD is then supplied to a system controller (not shown).

A guide portion 5 is protruded in the direction of insertion from a distal-end face of the insertion portion of the grip section 2B. When the rigid insert section 2A of the rigid endoscope 2 is inserted through the sheath insert section 3A of the washing sheath 3, the guide portion 5 is received in a guide connector 6 arranged on a sheath grip section 3B of the washing sheath 3. The rigid endoscope 2 and the washing sheath 3 are thus reliably connected to each other.

The washing sheath 3 includes the sheath insert section 3A and the sheath grip section 3B arranged on the proximal end side of the sheath insert section 3A. The sheath insert section 3A includes at an end portion of the sheath insert section 3A a nozzle 3b serving as an opening for supplying and sucking water. The insert section 2A is inserted through an insert channel 3c as an inner passage of the sheath insert section 3A.

The sheath grip section 3B includes at the proximal end thereof an opening 3D through which the insert section 2A of the rigid endoscope 2 is inserted into the insert channel 3C. The guide connector 6 is arranged on the circumference of the sheath grip section 3B close to the proximal end thereof. A socket portion 6b of the guide connector 6 is extended in perpendicular to the direction of insertion of the sheath grip section 3B. The guide connector 6 includes an opening 6a opening in the direction in which the insert section 2A of the rigid endoscope 2 is inserted. The socket portion 6b has a generally U-shape in plan view.

With this arrangement, when the insert section 2A of the rigid endoscope 2 is inserted through the insert channel 3c of the washing sheath 3, the guide portion 5 arranged on the grip section 2B of the rigid endoscope 2 is received in the guide connector 6 so that the washing sheath 3 and the rigid endoscope 2 are reliably connected to each other.

A guide portion 7 protruding in the direction of insertion is arranged on the distal end of the sheath grip section 3B. When the sheath insert section 3A of the washing sheath 3 is inserted through the wiper insert section 4A of the wiper sheath 4, the guide portion 7 is engaged with a guide connector 8 arranged on an operation unit 4B of the wiper sheath 4. In this way, the washing sheath 3 and the wiper sheath 4 are reliably connected to each other.

A water feed sleeve 3c to be in communication with the insert channel 3C is extended from the circumference of the sheath grip section 3B. One end of a water feed tube (not shown) is connected to the water feed sleeve 3c. The other end of the waver feed tube is connected to an injector serving as water feed means or sucking means.

A liquid such as a cleaning liquid cleaning the distal-end face 2a of the rigid endoscope 2 is fed to the water feed sleeve 3c via the water feed tube by the injector. Water is also sucked out by the injector. The water feed means is not limited to an injector. The water feed means may be a water feeder.

A nozzle 3b is arranged to a distal end portion 3a of the sheath insert section 3A. The nozzle 3b is formed by bending the distal end portion 3a inward. The bent area is waved. The nozzle 3b has a predetermined dimension so that the field of view of the rigid endoscope 2 is not narrowed, in other words, so that the observation window of the distal-end face 2a of the insert section 2A is not blocked.

With the insert section 2A of the rigid endoscope 2 inserted in the insert channel 3c, a slight distal end gap (not shown) remains between the inner circumference of the nozzle 3b and the distal-end face 2a of the insert section 2A.

With the insert section 2A of the rigid endoscope 2 inserted in the insert channel 3c, a slight gap serving as a liquid passage, namely, an insertion gap (see 3d of FIG. 16 and so on) remains between the inner circumference of the sheath insert section 3A and the outer circumference of the insert section 2A.

The distal end of the insertion gap 3d communicates with the distal end gap, and the proximal end of the insertion gap 3d communicates with the injector via the water feed sleeve 3C.

The opening 3D of the sheath grip section 3B is loaded at an adequate location thereof with an O-ring (not shown). With the insert section 2A inserted, the O-ring is tightened to the outer circumference of the insert section 2A, thereby maintaining water-tightness on the proximal end of the insertion gap 3d.

With this arrangement, the injector is operated with the insert section 2A of the rigid endoscope 2 inserted in the insert channel 3c of the sheath insert section 3A. A liquid is fed from within the injector to the distal-end face 2a of the insert section 2A from all radial directions via the water feed sleeve 3C, the insertion gap 3d, and the distal end gap of the nozzle 3b. The cleaning liquid thus cleans the distal-end face 2a.

Figure 2:
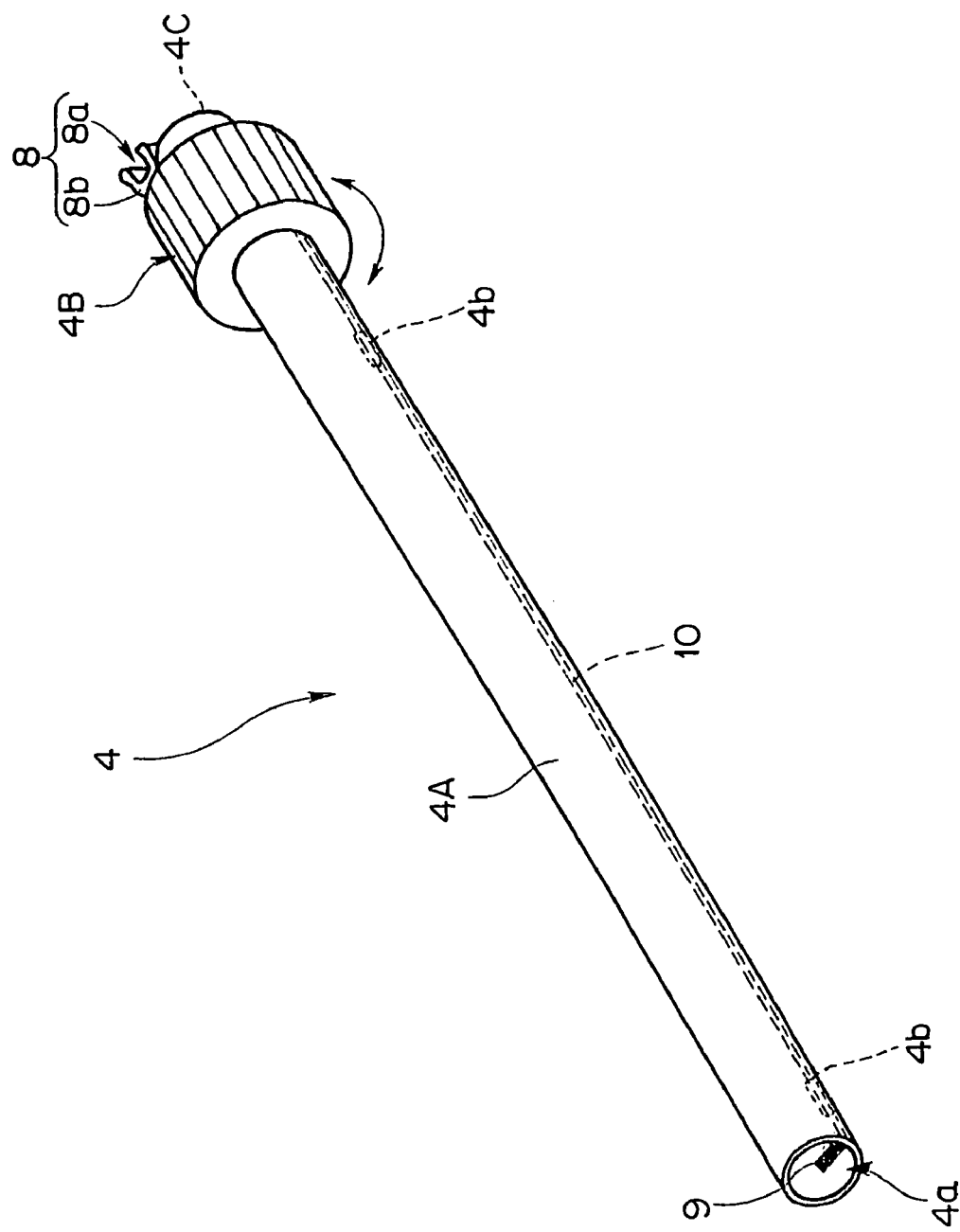
FIG. 2 is a perspective view illustrating a structure of a wiper sheath.

As shown in FIGS. 1 and 2, the wiper sheath 4 includes the wiper insert section 4A, a wiper 9 attached to the distal end of the wiper insert section 4A, and the operation unit 4B attached to the proximal end of the wiper insert section 4A. The sheath insert section 3A of the washing sheath 3 is inserted through the inner passage 4a of the wiper insert section 4A. The wiper 9 is used to wipe water ejected through the nozzle 3b to the distal-end face 2a of the insert section 2A or water or a body fluid sticking to the distal-end face 2a. The wiper 9 is arranged to be in contact with the distal-end face 2a of the insert section 2A within the sheath insert section 3A. The operation unit 4B is used to cause the wiper 9 to be in contact with the distal-end face 2a to wipe water or body fluid sticking to the distal-end face 2a. The operation unit 4B is also used to move the wiper 9 in an arc to a far position spaced apart from the distal-end face 2a. The wiper 9 is moved in an arc with respect to the distal-end face 2a so that the wiper 9 is prevented from being in contact with the nozzle 3b.

The operation unit 4B includes on the proximal end thereof an opening 4C through which the sheath insert section 3A of the washing sheath 3 is inserted. A guide connector 8 is arranged on the operation unit 4B close to the opening 4C.

The guide connector 8 is similar in structure to the guide connector 6 of the washing sheath 3. The guide connector 8 has an opening 8a opened in the direction in which the sheath insert section 3A of the washing sheath 3 is inserted. The guide connector 8 has a socket portion 8b having a generally U-shape in plan view.

When the sheath insert section 3A of the washing sheath 3 is inserted in the wiper sheath 4 in that arrangement, the guide portion 7 arranged on the sheath grip section 3B of the washing sheath 3 is received in and engaged with the guide connector 8. The wiper sheath 4 and the washing sheath 3 are thus reliably connected to each other.

A tubular holder 4b is arranged within the inner passage 4a of the wiper insert section 4A. A wiper shaft 10 integrally formed with the wiper 9 is supported rotatably and movably in an arc by the tubular holder 4b. A plurality of cutouts are made on the wiper insert section 4A. For example, one cutout is made on the distal end of the wiper insert section 4A and the other cutout is made on the proximal end of the wiper insert section 4A. The tubular holders 4b are respectively arranged in the cutouts. The holders 4b with the wiper shaft 10 passing therethrough are then laser welded to the wiper insert section 4A (see FIG. 29).

The wiper 9 is integrally formed with the end of the wiper shaft 10 using insert molding. The wiper 9, made of flexible rubber, has a generally rectangular shape having a size large enough to wipe the observation window of the distal-end face 2a and nearby. The wiper 9 is so thick that the wiper 9 in the bent state thereof is in contact with the distal-end face 2a to wipe water and body fluids sticking to the distal-end face 2a.

The proximal end of the wiper shaft 10 is arranged in the operation unit 4B. The operation unit 4B is operated by a surgeon to pivot the wiper 9. A drive force responsive to a pivotal motion by the surgeon is transferred to the wiper 9 via the wiper shaft 10. The operation unit 4B will be described later in more detail.

With the washing sheath 3 inserted in the wiper sheath 4 in this embodiment, the wiper 9 is placed into contact with the distal-end face 2a of the rigid endoscope 2 arranged within the washing sheath 3.

The endoscope system 1, including the rigid endoscope 2, the washing sheath 3 and the wiper sheath 4, is set to be inserted in a trocar (not shown) during a surgical operation. The endoscope system 1 in the trocar is held within the body of a patient, and an observation image of a region within the abdominal cavity of the patient captured through the observation optical system is supplied to a system controller via a camera head.

A specific structure of the operation unit 4B of the wiper sheath 4 is described below with reference to FIGS. 3 through 11.

In the endoscope system 1, the wiper 9 in the wiper sheath 4 wipes water and body fluids sticking to the distal-end face 2a of the rigid endoscope 2 set in the washing sheath 3. When the wiper 9 slides on the distal-end face 2a, the wiper 9 may touch the nozzle 3b of the washing sheath 3.

If the wiper 9 touches the nozzle 3b, the wiper 9 can be damaged. If the wiping area of the wiper 9 is narrowed to overcome such a problem, there is a possibility that water or body fluids may remain within the field of view of the distal-end face 2a.

The operation unit 4B forming the wiper sheath 4 in the endoscope system 1 of the embodiment is thus operated, wiping the water and the body fluids off the distal-end face 2a while moving the wiper 9 in an arc with respect to the distal-end face 2a away from the nozzle 3b.

Figure 3:
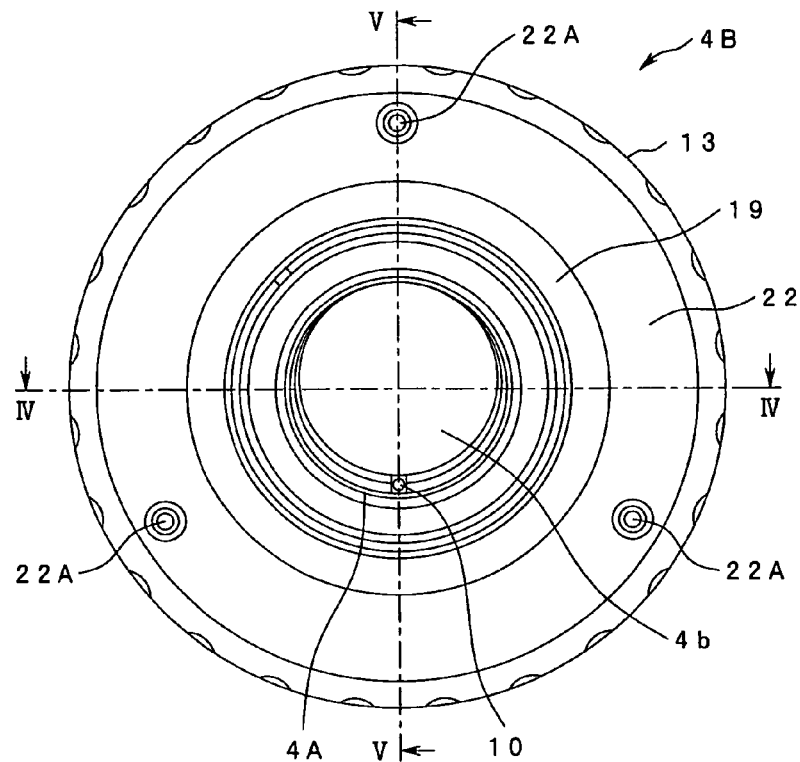
FIG. 3 is a front view of an operation unit arranged on the wiper sheath.
Figure 4:
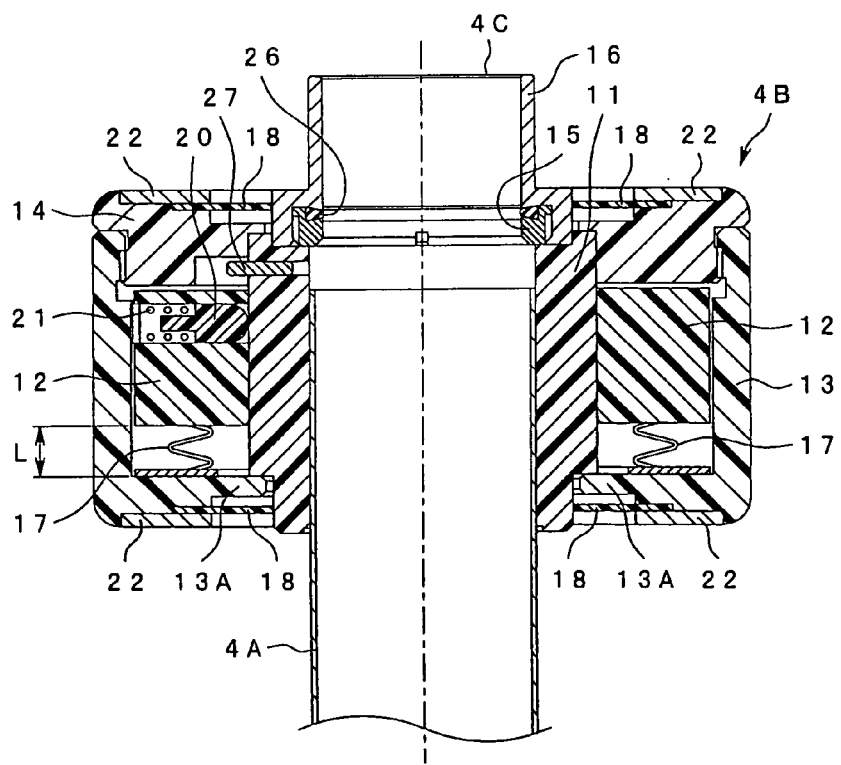
FIG. 4 is a sectional view of the operation unit taken along line IV-IV in FIG. 3.
Figure 5:
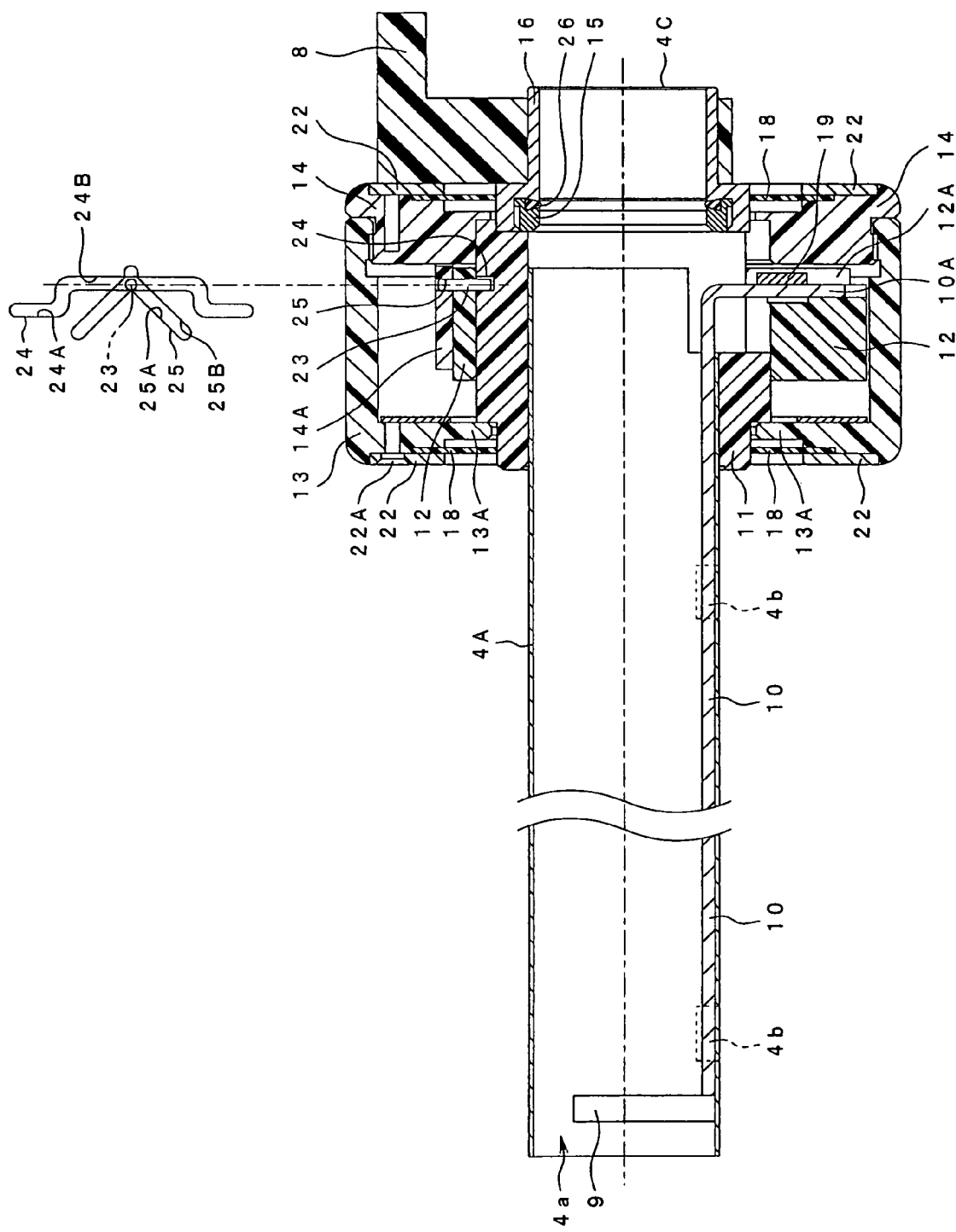
FIG. 5 is a sectional view of the operation unit taken along line V-V in FIG. 3.

The operation unit 4B of FIGS. 3 through 5 includes a tubular body 11, a wiper tube 12 supported rotatably and movably in an arc with respect to the body 11, a first rotary ring 13, a second rotary ring 14, and first and second O-ring holders 15 and 16 arranged on the proximal end of the body 11. The body 11 is secured to the proximal end of the wiper insert section 4A. The wiper tube 12 includes a recess portion 12A that locks a bent portion 10A of the wiper shaft 10 on the proximal end thereof. The wiper shaft 10 is supported rotatably and movably in an arc within the wiper insert section 4A. The first rotary ring 13 and the second rotary ring 14 house the body 11 and the wiper tube 12 within the inner circumferences thereof and are rotatably supported on the body 11. The first rotary ring 13 and the second rotary ring 14 are rotatable and movable in an arc in engagement with the wiper tube 12. The first and second O-ring holders 15 and 16 hold an O-ring 26 that maintains water-tightness in the proximal end of the wiper sheath 4 and the sheath insert section 3A of the washing sheath 3.

Figure 7:
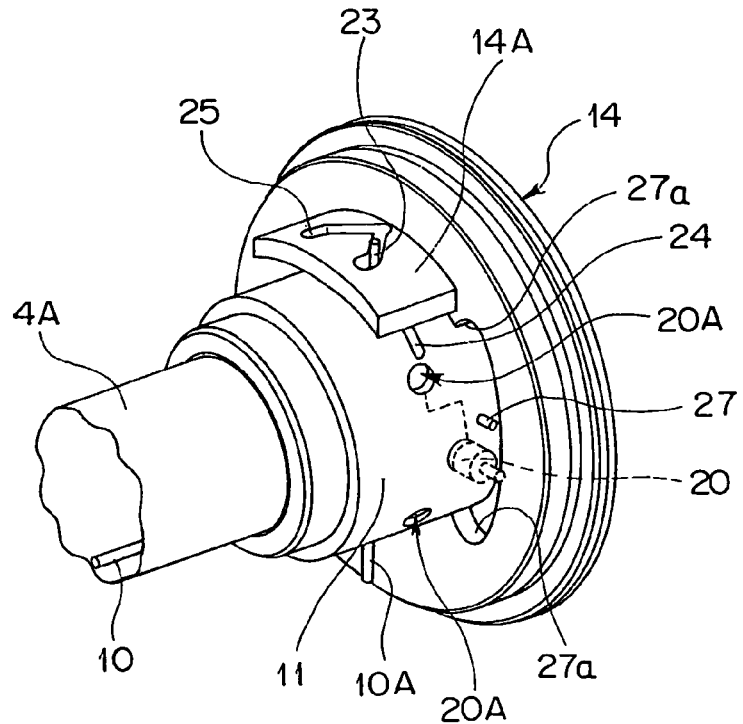
FIG. 7 is a perspective view illustrating the body of the rigid endoscope and the a second rotary ring.

As shown in FIGS. 5 and 7, two holes 20A and a first cam groove 24 are arranged on predetermined locations on the outer circumference of the body 11. The holes 20A restrains a rotary motion of the wiper tube 12. The first cam groove 24 restrains the longitudinal movement when the wiper tube 12 is pivoted. The specific shape of the first cam groove 24 will be described later.

The hole 20A receives a click pin 20 that is supported in a manner protrudable toward the inner circumference of the wiper tube 12 as shown in FIGS. 4 through 7. The click pin 20 is continuously urged toward the body 11 by a click spring 21 loaded within the wiper tube 12.

While the wiper tube 12 is pivoted, the click pin 20 is engaged with one of the holes 20A, and the pivotal motion of the wiper tube 12 is thus limited. More specifically, the wiper tube 12 is pivotally movable within a range defined between the two holes 20A as shown in FIG. 7.

The body 11 is provided with a stopper 27 at a predetermined location. When the stopper 27 abuts a stop position 27a of the second rotary ring 14 (see FIG. 7), the wiper tube 12 is prevented from further pivoting from a pivot limit position determined by the hole 20A and the click pin 20.

Figure 6:
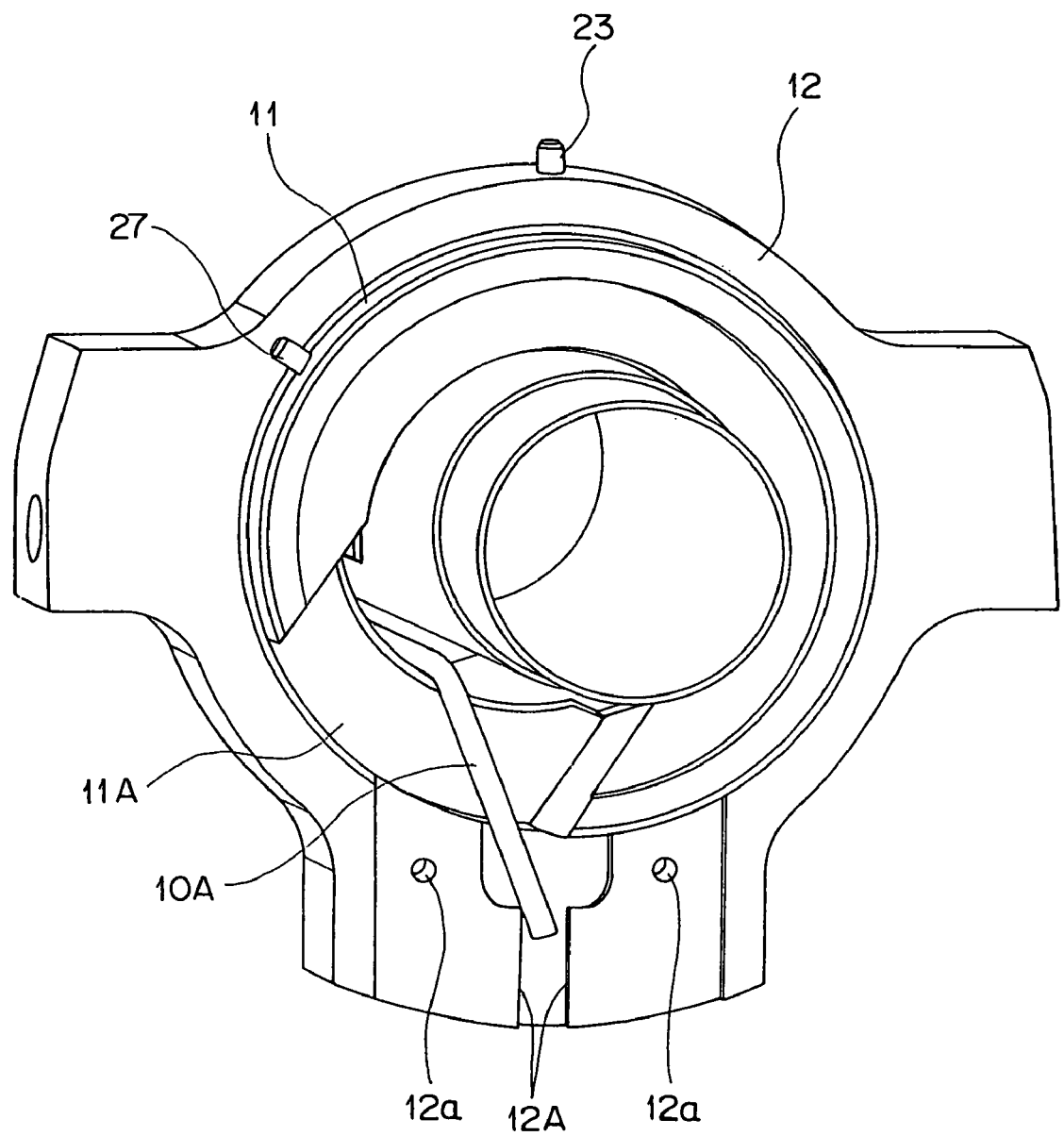
FIG. 6 is a perspective view illustrating a wiper tube engaged with a body of a rigid endoscope.

As shown in FIG. 6, the body 11 includes an allowance recess portion 11A having a predetermined width. The wiper shaft 10 is received in the allowance recess portion 11A. The allowance recess portion 11A receives the bent portion 10A of the wiper shaft 10 locked by the recess portion 12A of the wiper tube 12 while allowing the wiper tube 12 to rotate and move in an arc.

The bent portion 10A of the wiper shaft 10 is locked by the recess portion 12A of the wiper tube 12. Screw holes 12a are arranged on both side areas of the recess portion 12A. The recess portion 12A is covered with a wiper retraining member 19 with the bent portion 10A received in the recess portion 12A. The wiper retraining member 19 is secured to the body 11 by tightening screws (not shown) into the screw holes 12a.

This arrangement prevents the bent portion 10A of the wiper shaft 10 from coming off the recess portion 12A. The wiper shaft 10 can thus move in an arc along with the wiper tube 12.

A pin 23 is arranged at a predetermined location on the circumference of the wiper tube 12. The pin 23 is operatively engaged with the first cam groove 24 of the body 11 and a second cam groove 25 arranged on an extension portion 14A of the second rotary ring 14. The pin 23 thus guides the wiper tube 12 in the rotation and longitudinal movement thereof.

As shown in FIG. 5, the pin 23 passing through the wiper tube 12 at a predetermined location with one end protruding from the outer circumference of the wiper tube 12 by a predetermined length and the other end inwardly protruding from the inner circumference of the wiper tube 12 by a predetermined length. The one end of the pin 23 protruding from the outer circumference of the wiper tube 12 is received in the second cam groove 25 while the other end of the pin 23 inwardly protruding from the inner circumference of the wiper tube 12 is received in the first cam groove 24. The shape of the second cam groove 25 will be specifically described later.

Figure 8:
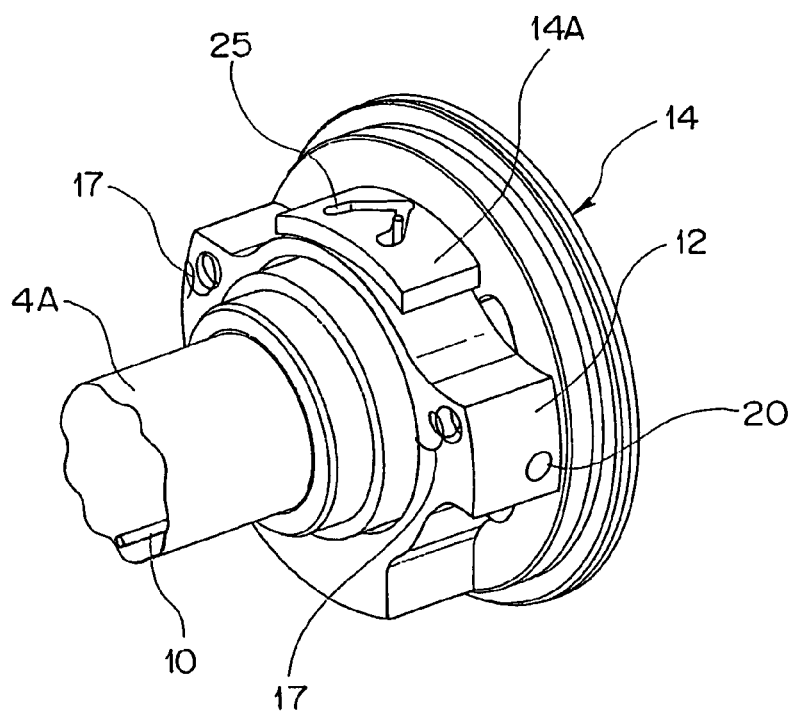
FIG. 8 is a perspective view of the wiper tube of FIG. 6 attached to the body of the rigid endoscope and the second rotary ring of FIG. 7.

As shown in FIGS. 4 and 8, the wiper tube 12 is urged toward the proximal end of the wiper sheath 4 by at least two springs 17. The urging force of the springs 17 and the urging force of the wiper 9 are related as below. The urging force of the wiper 9 occurs when the wiper 9 is in contact with the distal-end face 2a, and works in the direction of insertion of the wiper sheath 4.

Urging Force of the Springs 17>Urging Force of the Wiper 9

With this relationship satisfied, the pin 23 is reliably engaged with the first cam groove 24 and the second cam groove 25. The wiper tube 12 can thus perform the pivotal operation and the longitudinal movement operation in accordance with the shapes of the cam grooves 24 and 25.

The extension portion 14A having the second cam groove 25 as shown in FIGS. 5 through 8 is integrally formed with the second rotary ring 14. The extension portion 14A is extended in the direction of insertion from the second rotary ring 14 at a predetermined location thereof.

As shown in FIGS. 7 and 8, the second rotary ring 14, housing the body 11 and the wiper tube 12 with the pin 23 received in the second cam groove 25 of the extension portion 14A, is assembled to the first rotary ring 13.

Figure 9:
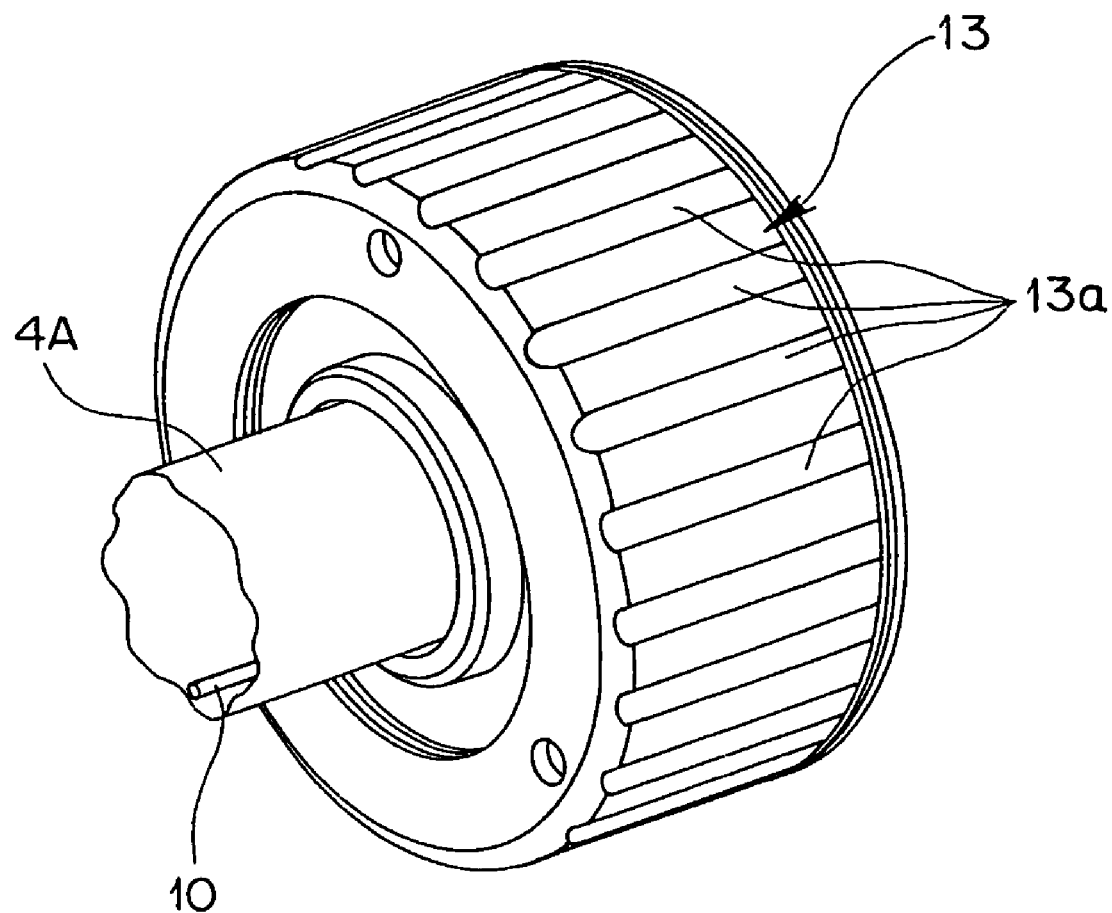
FIG. 9 is a perspective view illustrating a first rotary ring.

As shown in FIG. 9, the first rotary ring 13 forms an outer housing of the operation unit 4B to be rotated by a surgeon. The first rotary ring 13 has on the outer circumference knurled with a plurality of grooves 13a to help the surgeon to grip and rotate easily the first rotary ring 13.

A fixing section 13A is arranged on the distal-end face of the first rotary ring 13. A ring-like seal member 18 is loaded onto the fixing section 13A to maintain water-tightness in the interior of the first rotary ring 13. The seal member 18 is integrally secured to the first rotary ring 13 by tightening a screw 22A onto a fixing plate 22.

Similarly, a ring-like seal member 18 is arranged on the proximal end of the second rotary ring 14. The seal member 18 is secured to the second rotary ring 14 into a unitary body by screw tightening a fixing plate 22.

The guide connector 8 is arranged on the outer circumference of the second O-ring holder 16. The guide connector 8 is secured to the second O-ring holder 16 into a unitary body.

Next, the shapes of the first cam groove 24 and the second cam groove 25 are described below with reference to FIG. 10.

The second cam groove 25 receiving one end of the pin 23 is a generally V slot formed in the extension portion 14A.

The generally V shaped second cam groove 25 includes a second distal guide face 25A forming the distal-end side and a second proximal guide face 25B forming the proximal-end side.

On the other hand, the first cam groove 24 receiving the other end of the pin 23 has a generally crank shape.

The generally crank shaped first cam groove 24 includes a first distal guide face 24A forming the distal-end side and a first proximal guide face 24B forming the proximal-end side. The wiper tube 12 is continuously urged by the springs 17 toward the proximal end of the wiper sheath 4. Thus, the pin 23 is received in the first cam groove 24 in engagement with the first proximal guide face 24B.

The pin 23 is guided in accordance with the shapes of the first cam groove 24 and the second cam groove 25. Thus, the wiper tube 12 having the pin 23 fixed thereon is integrally moved with the pin 23. The wiper shaft 10 having the bent portion 10A received in the groove portion 12A of the wiper tube 12 is thus rotated and moved in an arc.

When the wiper tube 12 with the bent portion 10A of the wiper shaft 10 fixed thereon is moved, the wiper shaft 10 is rotated and moved in an arc. Then, along with the wiper shaft 10, the wiper 9 fixed to the wiper shaft 10 performs a wiping operation to wipe the distal-end face 2a, and a retraction operation in which the wiper 9 is retracted from the nozzle 3b of the washing sheath 3 by spacing apart from the distal-end face 2a in a distant direction.

Figure 10:
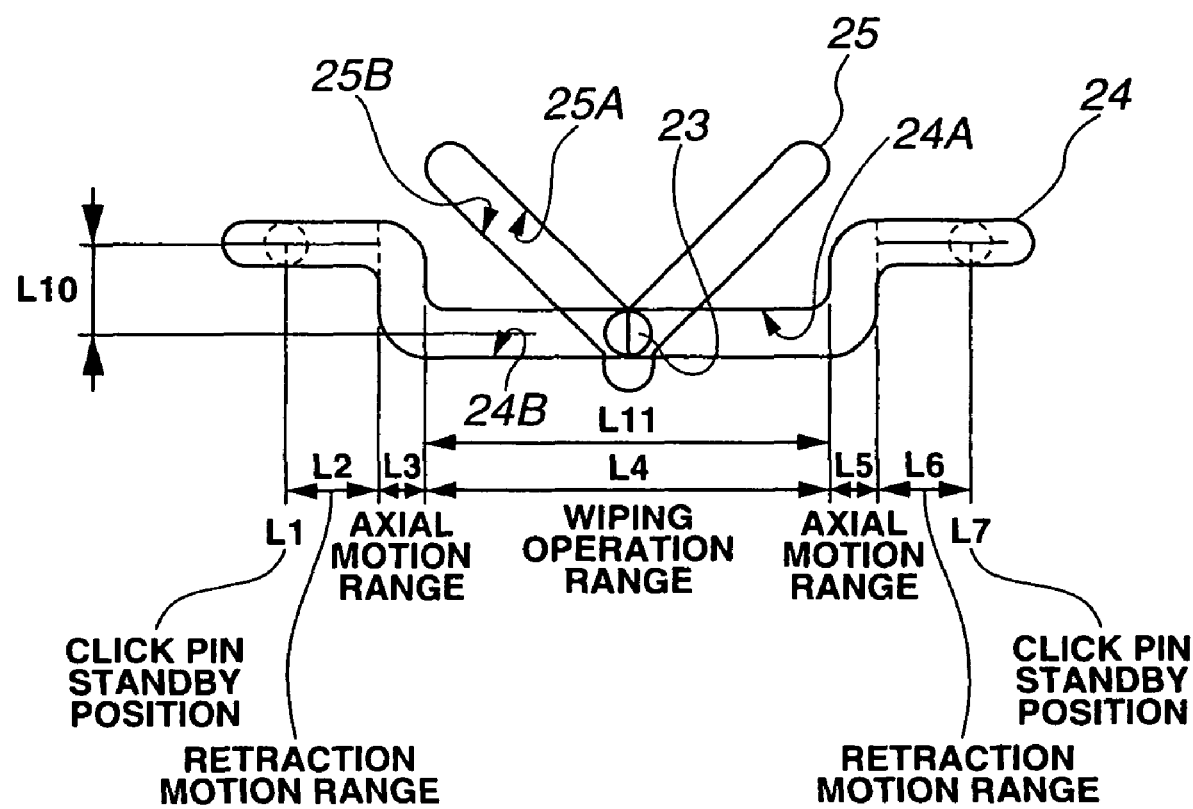
FIG. 10 illustrates a first cam groove arranged on the body of the rigid endoscope and a second cam groove arranged on the second rotary ring.

FIG. 10 illustrates the relationship between the position of the pin 23 in the first cam groove 24 and the operation of the wiper 9.

As shown in FIG. 10, when the pin 23 is placed to one of positions L1 and L7 near the ends of the first cam groove 24, the click pin 20 is received in the hole 20A to put the wiper 9 to a standby state. The positions L1 and L7 are click pin standby positions.

With the position L1 set as a wiping operation start point, the position L7 becomes a wiping operation end point at which the wiper tube 12 completes a wiping operation after traveling a predetermined direction, and the position L7 then serves as a start point for a next wiping operation.

When the pin 23 is placed in one of ranges L2 and L6 of the first cam groove 24, the wiper 9 is shifted to a far position from the distal-end face 2a, thus, spaced apart from the nozzle 3b of the washing sheath 3. The ranges L2 and L6 are retraction ranges within which the wiper 9 is retracted from the observation field of view.

When the pin 23 falls within one of ranges L3 and L5 of the first cam groove 24, the wiper 9 moves in the axial direction. That is, the ranges L3 and L5 are ranges within which the wiper 9 is axially moved. When the pin 23 is moved downward in FIG. 10, the wiper 9 moves from the far position to be in contact with the distal-end face 2a. In contrast, when the pin 23 is moved upward in FIG. 10, the wiper 9 is shifted from the contact state with the distal-end face 2a to the far position.

When the pin 23 is placed within a wiping operation range L4 of the first cam groove 24, the wiper 9 slides on the distal-end face 2a, namely, wipes water and body fluids of the distal-end face 2a. The range L4 is a wiping operation range within which the wiper 9 wipes the fluids.

The distance of the wiper 9 to the far position is determined by a length L10, and a wiping range of the wiper 9 is determined by a length L11.

Operation of the endoscope system 1 of the present embodiment is described below with reference to FIGS. 12 through 24.

Figure 12:
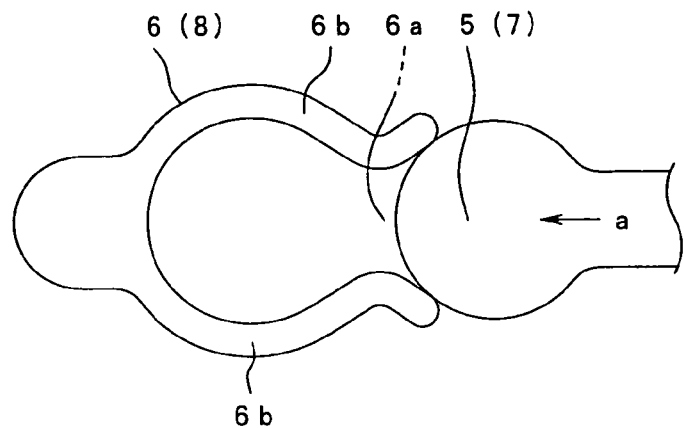
FIG. 12 illustrates a state that a guide of a rigid endoscope 2 is in contact with an opening of the guide connector of a washing sheath or a wiper sheath.

Assembling of the endoscope system 1 is described with reference to FIGS. 12 through 14.

The insert section 2A of the rigid endoscope 2 of FIG. 1 is inserted through the sheath insert section 3A of the washing sheath 3. As shown in FIG. 12, the guide portion 5 of the rigid endoscope 2 moving in the distal direction (as represented by an arrow "a") is then brought into contact with the opening 6a of the socket 6 forming the guide connector 6 of the washing sheath 3.

Figure 13:
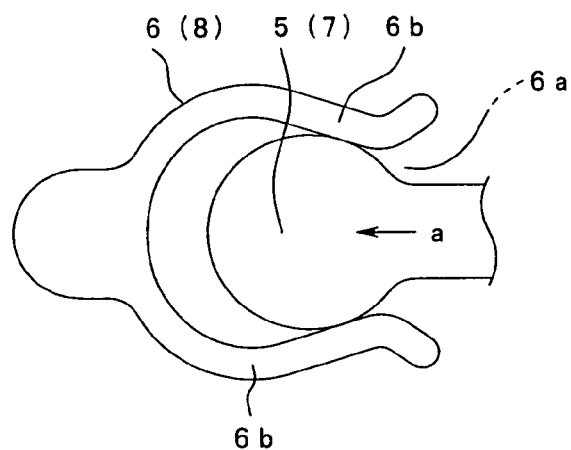
FIG. 13 illustrates the guide that is being inserted into the guide connector.
Figure 14:
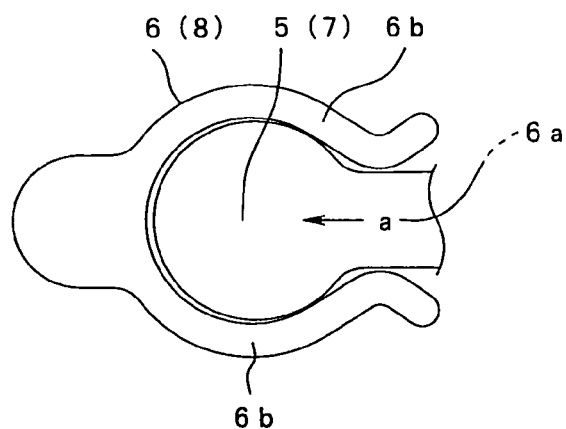
FIG. 14 illustrates the guide connector and the guide in the engagement state thereof.

When the insert section 2A of the rigid endoscope 2 is further moved in the direction represented by the arrow "a", the guide portion 5 widens open the socket 6b of the guide connector 6 and then enters inside the socket 6 as shown in FIG. 13. With the insert section 2A further moved in the direction of the arrow "a", the guide portion 5 is fully engaged with the guide connector 6 as shown in FIG. 14. Thus, the washing sheath 3 and the rigid endoscope 2 are reliably connected to each other.

The sheath insert section 3A of the washing sheath 3 having the rigid endoscope 2 remaining inserted therethrough is inserted into the wiper insert section 4A of the wiper sheath 4.

In the same way as with the relationship between the guide portion 5 and the guide connector 6, the guide portion 7 of the washing sheath 3 is mated with the guide connector 8 of the wiper sheath 4. As a result, the washing sheath 3 and the wiper sheath 4 are reliably connected to each other, and the endoscope system 1 is now assembled.

Next, operation of the wiper 9 in response to the operation of the operation unit 4B of the endoscope system 1 is described below with reference to FIGS. 10 and 15 through 24.

First, a surgeon now rotates the operation unit 4B of the wiper sheath 4 in the endoscope system 1 to perform a wiping operation of the wiper 9.

Figure 15:
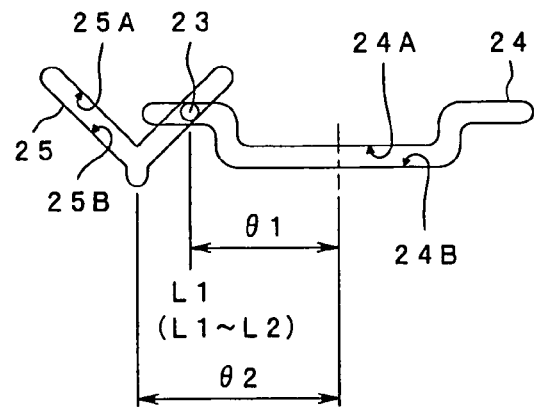
FIG. 15 illustrates the relationship between the first cam groove and the second cam groove with a pin positioned at a click pin standby position L1 of the first cam groove.
Figure 16:
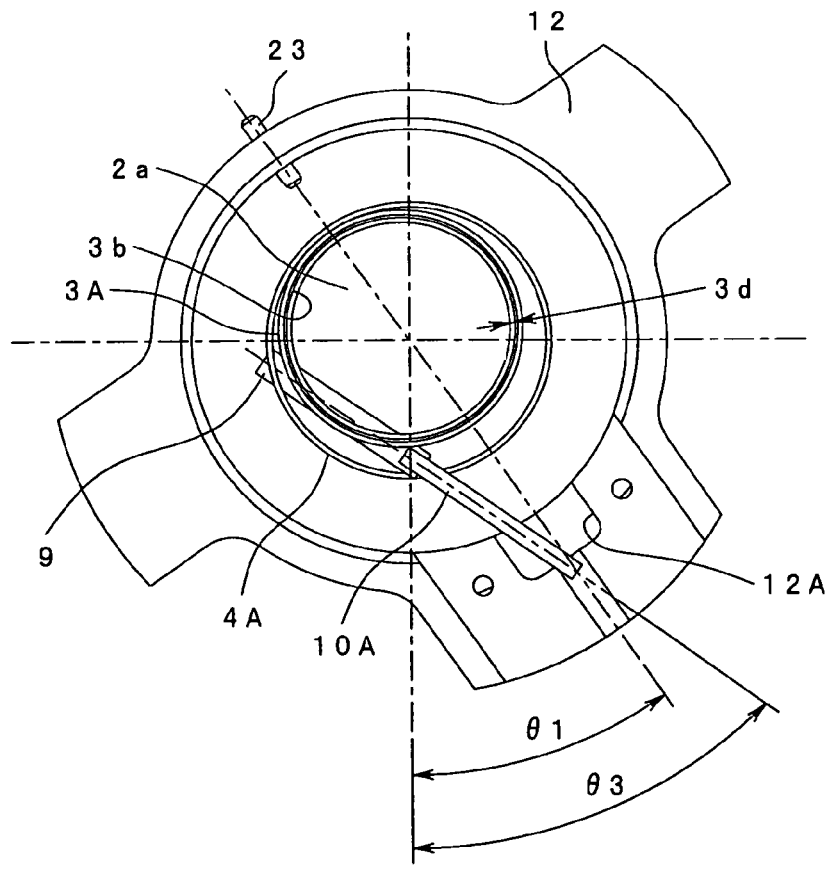
FIG. 16 illustrates a wiper tube in a rotation state thereof and a wiper in an initial operation state thereof with the pin position at the location of FIG. 15.

In this case, as shown in FIG. 15, the pin 23 is positioned at the click pin standby position L1 of the first cam groove 24. The click pin standby position L1 is an initial position, and the wiper tube 12 in the operation unit 4B remains at an angle of rotation $\theta 3$ as shown in FIG. 16. The pin 23 makes an angle of $\theta 1$ with respect to the first cam groove 24, and the pin 23 makes an angle of $\theta 2$ with respect to the second cam groove 25.

When the pin 23 is at the click pin standby position L1, the wiper 9 of FIG. 16 is placed at the retraction position out of the observation field of view without being in contact with the nozzle 3b of the washing sheath 3.

The surgeon rotates the operation unit 4B clockwise to perform the wiping operation. Then, the pin 23 moves in accordance with the first cam groove 24 and the second cam groove 25. More specifically, the pin 23 moves from the click pin standby position L1 to the axial motion range L3 via the retraction motion range L2 of the first cam groove 24 as shown in FIG. 17.

Since the wiper tube 12 is continuously urged toward the proximal end side of the wiper sheath 4 by the springs 17, the pin 23 moves from the click pin standby position L1 to within the retraction motion range L2, sliding along the first proximal guide face 24B of the first cam groove 24.

Thus, the wiper 9 is now approaching the distal-end face 2a from the far position spaced apart from the nozzle 3b of the washing sheath 3.

Figure 17:
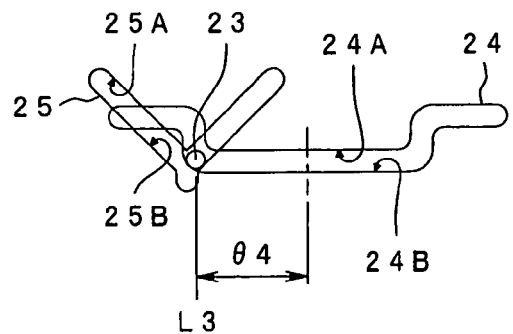
FIG. 17 illustrates the relationship between the first cam groove and the second cam groove when the pin shifts to within an axial motion range L3 via a retraction motion range L2 of the first cam groove.
Figure 18:
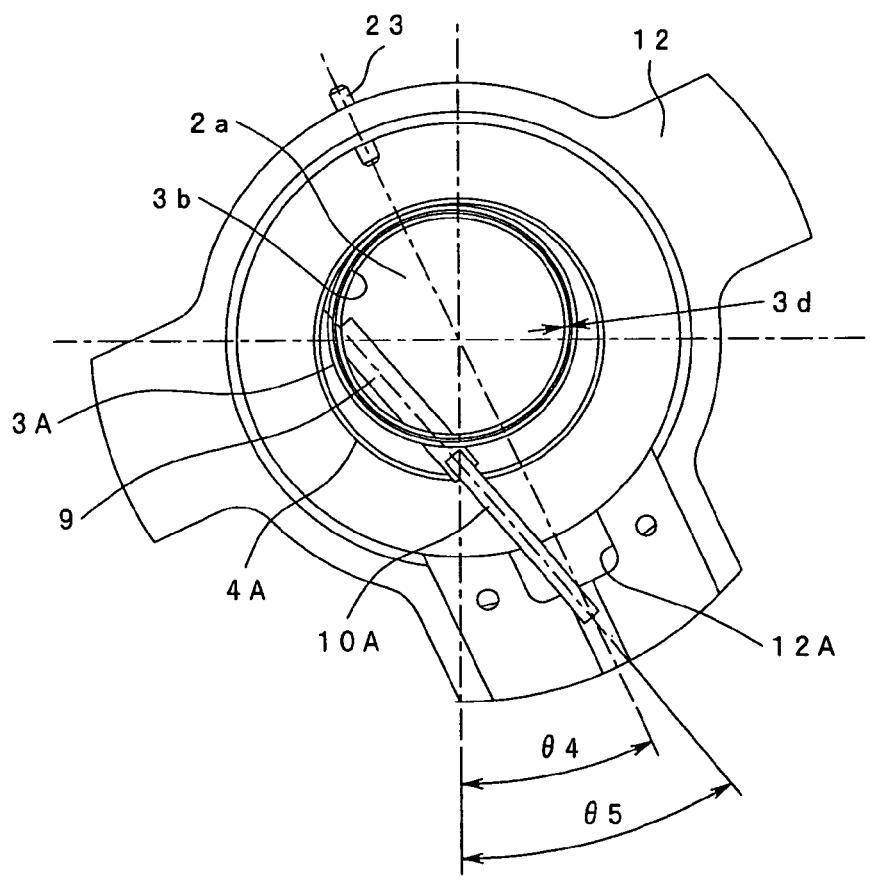
FIG. 18 illustrates the wiper tube in the rotation state thereof and the wiper in an axial motion state thereof with the pin positioned at the location of FIG. 17.

When the pin 23 is placed within the axial motion range L3 as shown in FIG. 17, the wiper tube 12 within the operation unit 4B is placed at an angle $\theta 5$ smaller than the previous angle $\theta 3$ as shown in FIG. 18. The angle of the pin 23 with respect to the first cam groove 24 becomes a angle $\theta 4$ smaller than the previous angle $\theta 1$.

That is, when the pin 23 is placed to within the axial motion range L3, the wiper tube 12 is moved toward the proximal end of the wiper sheath 4 by the urging force of the springs 17 along the linear portion of the first cam groove 24. As a result, the wiper 9 is brought into contact with the distal-end face 2a.

The surgeon further rotates the operation unit 4B, thereby causing the pin 23 to move along the wiping operation range L4 of the first cam groove 24.

Figure 19:
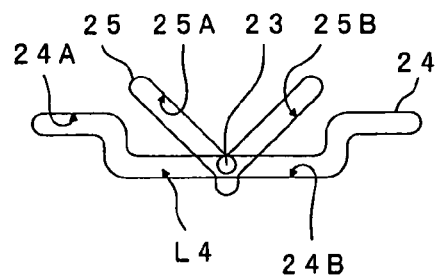
FIG. 19 illustrates the relationship between the first cam groove and the second cam groove with the pin positioned in a wiping operation range L4 of the first cam groove.

Then, as shown in FIG. 19, the pin 23 moves within the wiping operation range L4 in response to the rotation of the operation unit 4B, thereby sliding along the second proximal guide face 25B of the second cam groove 25 and the first proximal guide face 24B of the first cam groove 24.

Figure 20:
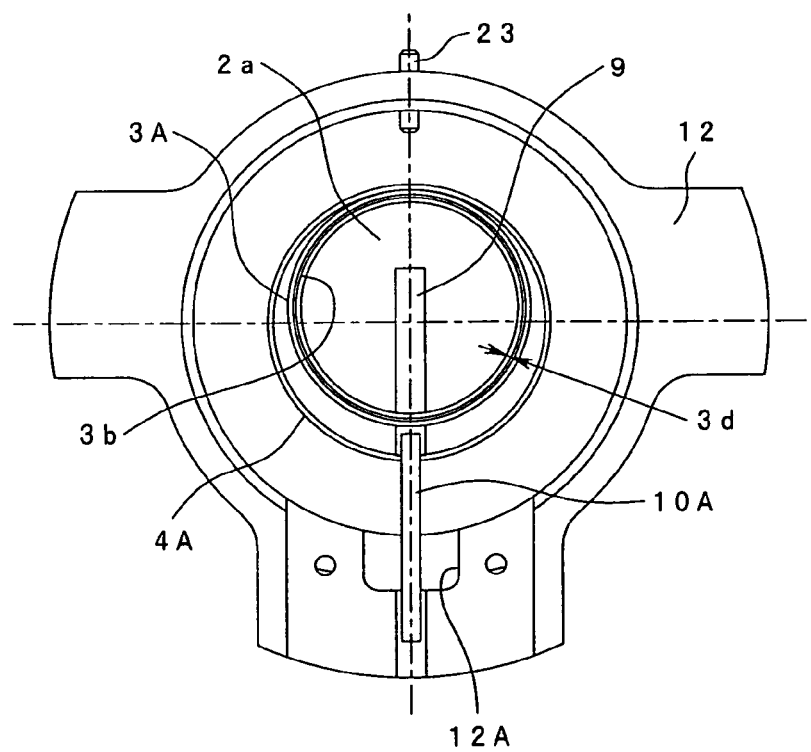
FIG. 20 illustrates the wiper tube in the rotation state thereof and the wiper in a wiping operation state thereof with the pin positioned at the location of FIG. 19.
Figure 21:
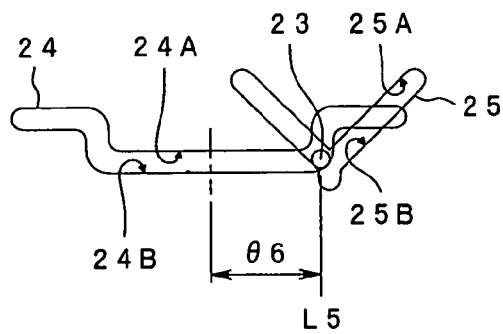
FIG. 21 illustrates the relationship between the first cam groove and the second cam groove with the pin positioned in the axial motion range L5.
Figure 22:
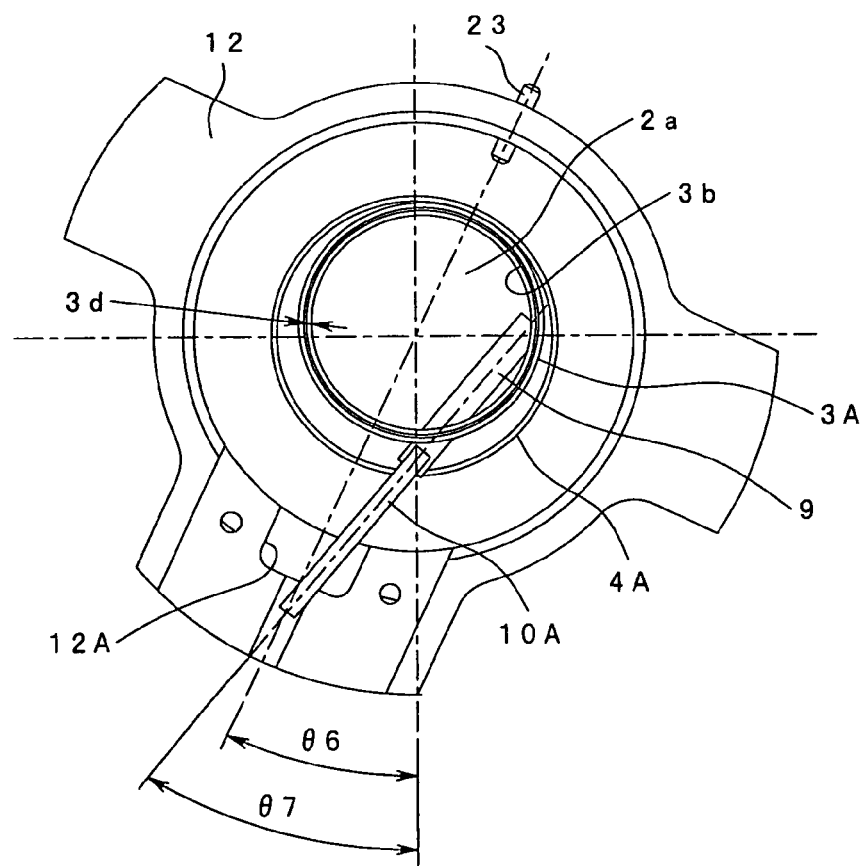
FIG. 22 illustrates the wiper tube in the rotation state thereof and the wiper in the axial motion state thereof with the pin positioned at the location of FIG. 21.
Figure 23:
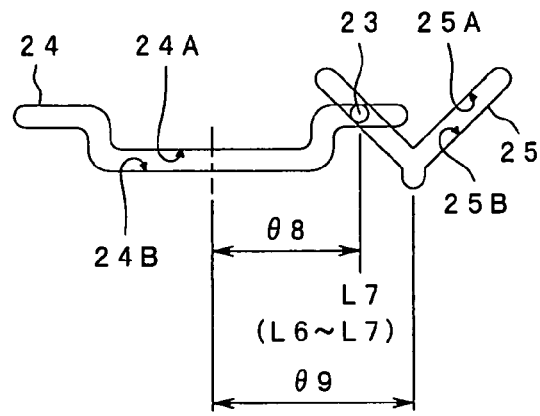
FIG. 23 illustrates the relationship between the first cam groove and the second cam groove when the pin is shifted to a click pin standby position L7 via a retraction motion range L6 of the first cam groove.

As shown in FIG. 20, the wiper tube 12 rotates with the pin 23 remaining at the position at the end of the axial motion range L3. In other words, the wiper 9 wipes the distal-end face 2a while moving in contact with the distal-end face 2a.

That is, the wiper 9 performs the wiping operation within the wiping operation range L4. Thus, the wiper 9 wipes water and body fluids off the distal-end face 2a, thereby assuring a good field of view.

Cleaning operation of the nozzle 3b of the washing sheath 3 may be performed throughout or in the middle of the rotation operation of the operation unit 4B. A cleaning fluid is ejected through the nozzle 3b. By performing the cleaning operation along with the wiping operation of the wiper 9, water and the body fluid are efficiently removed.

When the operation unit 4B is further clockwise rotated, the pin 23 slides along the first cam groove 24 and the second cam groove 25, thereby shifting from the wiping operation range L4 to within the axial motion range L5.

When the pin 23 is placed within the axial motion range L5, the wiper tube 12 within the operation unit 4B is placed at an angle $\theta 7$. And the angle of the pin 23 with respect to the first cam groove 24 becomes an angle $\theta 6$.

That is, within the axial motion range L5, the wiper tube 12 is shifted in the distal direction of the wiper sheath 4 contrary to the motion within the axial motion range L3. More specifically, the wiper 9 is shifted from the contact state thereof with the distal-end face 2a to the far position spaced apart from the distal-end face 2a. The wiper 9 is now detached from the distal-end face 2a.

When the surgeon further clockwise rotates the operation unit 4B, the pin 23 is shifted from the axial motion range L5 to the click pin standby position L7 via the retraction motion range L6 in the first cam groove 24 and the second cam groove 25.

When the pin 23 is shifted from the retraction motion range L6 to the click pin standby position L7, the wiper tube 12 is urged toward the proximal end of the wiper sheath 4 by the springs 17. The pin 23 thus moves being in contact with the first proximal guide face 24B of the first cam groove 24.

The wiper 9 thus goes out of the observation field of view in the state detached from the nozzle 3b of the washing sheath 3. In other words, the wiper 9 becomes a retraction state moving to the far position from the distal-end face 2a.

And, the pin 23 reaches the click pin standby position L7 in the first cam groove 24 and the second cam groove 25. This completes the wiping operation of the wiper 9 responsive to the clockwise rotation of the operation unit 4B.

Figure 24:
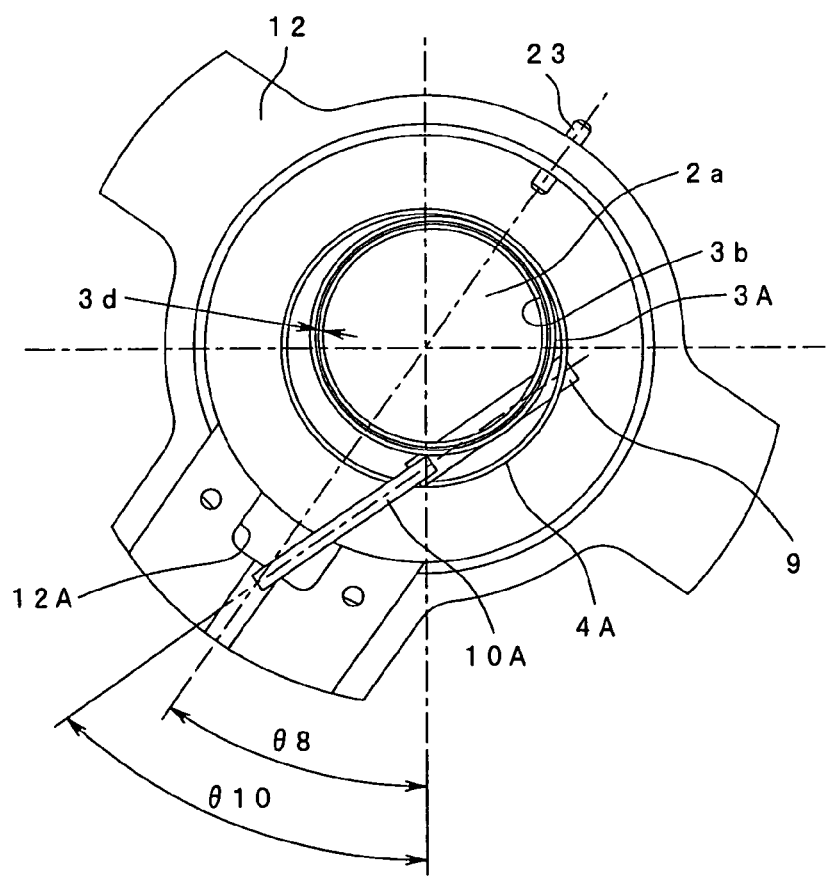
FIG. 24 illustrates the wiper tube in the rotation state thereof and the wiper in the operation end state thereof with the pin positioned at the location of FIG. 23.

The wiper tube 12 within the operation unit 4B is now held at an angle θ10 as shown in FIG. 24. The pin 23 has an angle θ8 with respect to the first cam groove 24, and an angle θ9 with respect to the second cam groove 25.

And, when the pin 23 is placed at the click pin standby position L7, the nozzle 3b of the washing sheath 3 remains out of reach of the wiper 9 as shown in FIG. 24. The wiper 9 stays at the retraction position thereof out of the observation field of view.

If a single stroke of the wiper 9 is not sufficient to clean dirt, the surgeon may counterclockwise rotate the operation unit 4B. The above-described process of the wiper 9 is reversed.

If the clockwise and counterclockwise rotations of the operation unit 4B are repeated, the wiper 9 wipes water and body fluids off the distal-end face 2a more sufficiently, and a sufficient field of view is thus assured.

With such a configuration of the endoscope apparatus, when the wiper 9 wipes the distal-end face 2a of the rigid endoscope 2, the wiper 9 is spaced apart from the nozzle 3b at the far position thereof separated from the distal-end face 2a. After the wiping operation starts, the wiper 9 is brought into contact with the distal-end face 2a. This arrangement allows the wiping area of the wiper 9 with respect to the distal-end face 2a to be maximized. The water and the body fluids sticking to the distal-end face 2a are efficiently wiped and removed. An excellent field of view is thus assured.

Since the wiper 9 slides on a desired area of the distal-end face 2a without being in contact with the nozzle 3b of the washing sheath 3, the wiper 9 maintains a wiping performance in a manner free from damage for a long period of time. Since the wiper 9 remains free from contact with the nozzle 3b, the force of the wiper 9 is easily adjusted.

When the endoscope system 1 is inserted into the abdominal cavity through a trocar, there is a possibility that an insufflation gas supplied into the abdominal cavity, blood, or a body fluid may leak out through the gap of the wiper sheath 4 and the operation unit 4B.

For this reason, the endoscope system 1 has an air-tight mechanism to prevent the insufflation gas and the body fluid from leaking out through the operation unit 4B.

The air-tight mechanism of the endoscope system 1 is described below with reference to FIGS. 5 and 11. As shown in FIG. 5, the endoscope system 1 includes the wiper shaft 10 within the wiper sheath 4 as shown in a lower portion of FIG. 5. By reason of this, the rotation axis of the wiper shaft 10 is offset from the center axis of the wiper insert section 4A of the wiper sheath 4.

This structure presents difficulty in maintaining water-tightness with the wiper 9 function. If the wiper sheath 4 including the wiper shaft 10 is water-tight sealed, a required torque of the wiper shaft 10 becomes large, thereby making operation difficult.

It is contemplated that water-tightness is assured by placing an O-ring between the operation unit 4B and the wiper insert section 4A. With such an arrangement, however, a required torque for the operation of the operation unit 4B becomes also large, making the rotation difficult.

The endoscope system 1 of the present embodiment employs a ring-shaped and sheet seal member 18.

The seal member 18 has an opening having a diameter equal to or slightly smaller than the outer diameter of the body 11. Two seal members 18 are respectively arranged on the proximal end of the body 11 and the distal end of the body 11. The seal members 18 are respectively secured to the first rotary ring 13 and the second rotary ring 14 to the predetermined state by tightening the screws 22a onto the fixing plates 22.

Portions of the seal members 18 in contact with the outer circumference of the body 11 are preferably deformed to be tightly in contact with the body 11 on the proximal end and the distal end of the operation unit 4B. Alternatively, the seal members 18 may be in contact with the outer circumference of the body 11 without being deformed.

The use of the two seal members 18 allows the first rotary ring 13 and the second rotary ring 14, namely, the interior of the operation unit 4B to be water-tight sealed. This arrangement prevents the insufflation gas and the body fluid, which may flow out from within the abdominal cavity, from being leaked through the operation unit 4B.

The seal members 18 are ring-shaped sheets serving as a water-tight member. Therefore, the torque required for the rotation operation of the operation unit 4B is not increased, and a small torque is sufficient to rotate the operation unit 4B.

Further, the endoscope system 1 employs an O-ring 26 in areas free from the rotation motion of the operation unit 4B to improve water-tightness.

Figure 11:
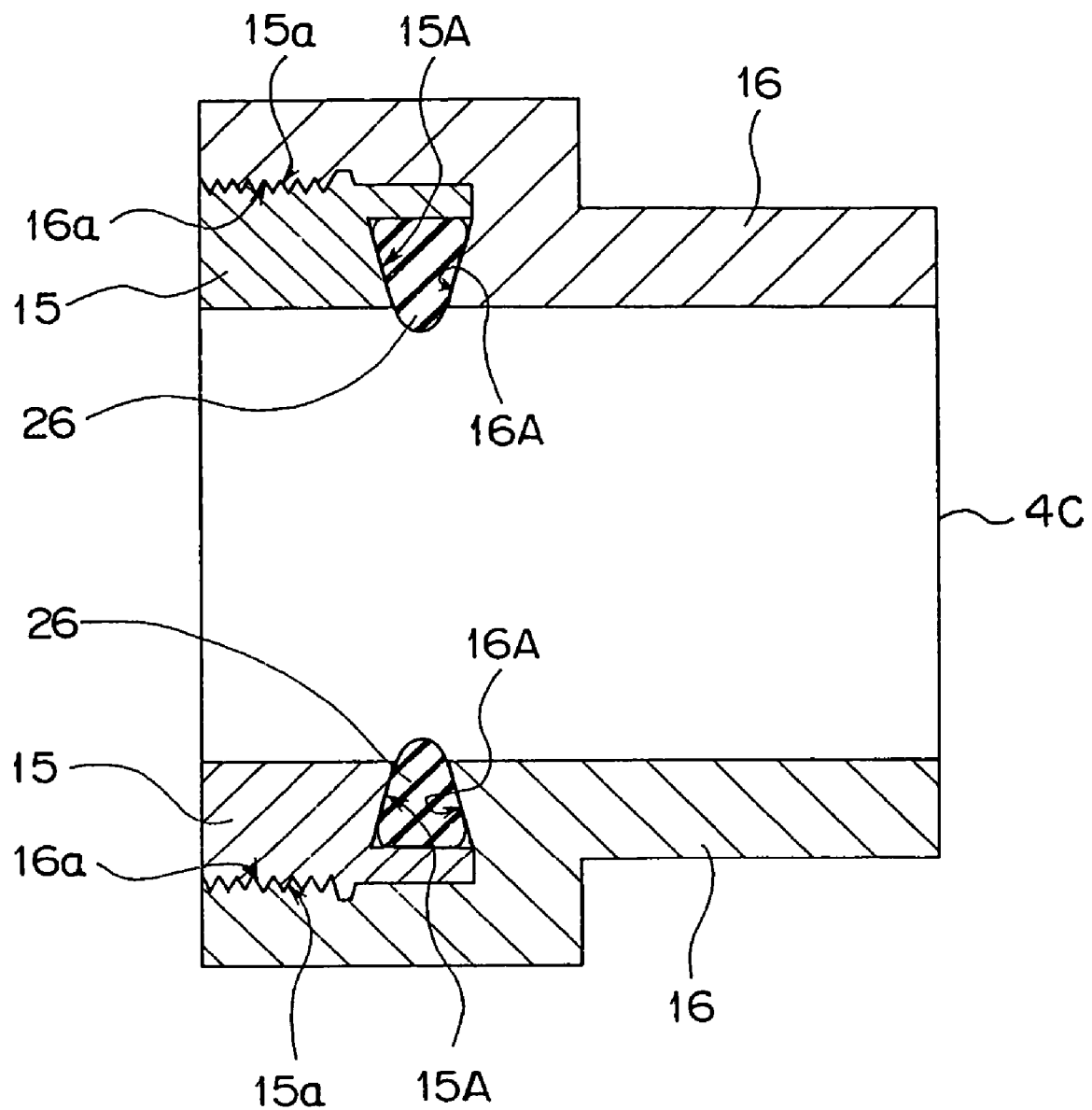
FIG. 11 is a sectional view of a seal structure including a first ring holder, a second ring holder, and an O-ring.

As shown in FIG. 11, the O-ring 26 is held between the first O-ring holder 15 and the second O-ring holder 16, and fixed within the second rotary ring 14.

In this arrangement, the first O-ring holder 15 has a male thread on outer circumference 15a on the distal end thereof. Meanwhile, the second O-ring holder 16 has a female thread on inner circumference 16a on the distal end thereof to be mated with the male thread on outer circumference 15a.

The first O-ring holder 15 has as the proximal end thereof a circular groove 15A that receives the O-ring 26. Meanwhile, the second O-ring holder 16 has, at a step on the inner circumference thereof, an abutment portion 16A engaging the O-ring 26. That is, the O-ring 26 is thus squeezed between the circular groove 15A and the abutment portion 16A. The O-ring 26 is deformed to be uniformly protruded to the center axis of the second O-ring holder 16.

The O-ring 26, which is deformed under the pressure between the first O-ring holder 15 and the second O-ring holder 16, is pressed into contact with the outer circumference of the sheath insert section 3A to be inserted through the inner passage 4b of the wiper sheath 4. Water-tightness is thus assured. This arrangement prevents the insufflation gas and the body fluid from leaking out through the wiper insert section 4A.

The wiper sheath 4 includes the wiper 9 in the endoscope system 1. Preferably, the wiper sheath 4 is easily inserted into the abdominal cavity of the subject and the wiper 9 is protected.

Figure 25:
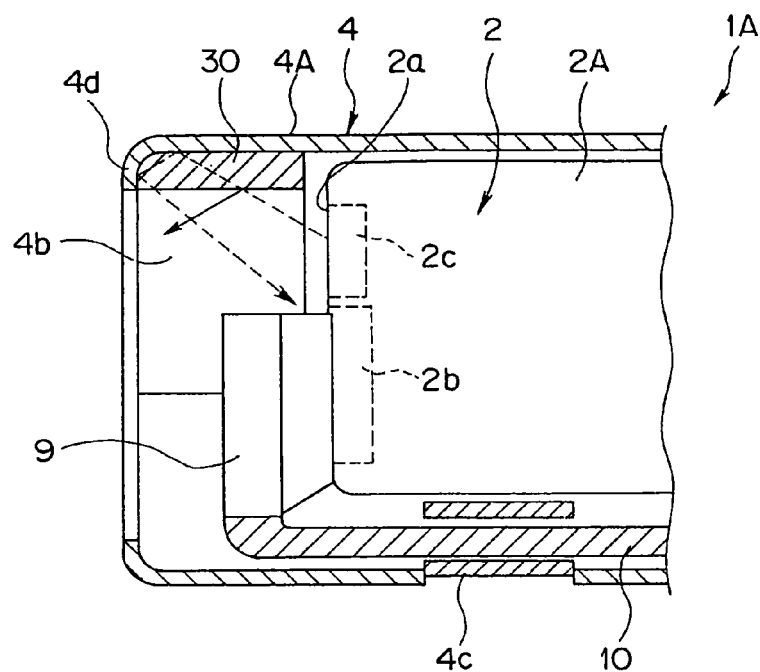
FIG. 25 is a sectional view of another example of an end portion of a wiper sheath forming the endoscope system.

As shown in FIG. 25, the wiper sheath 4 in an endoscope system 1A of one embodiment of the present invention is rounded at the distal end portion thereof as a rounded end portion 4d to facilitate insertion and to protect the wiper 9.

The tubular holder 4c is arranged in the wiper insert section 4A of the wiper sheath 4 to support the wiper shaft 10 in a manner that allows the wiper shaft 10 to be rotated and axially moved.

Figure 29:
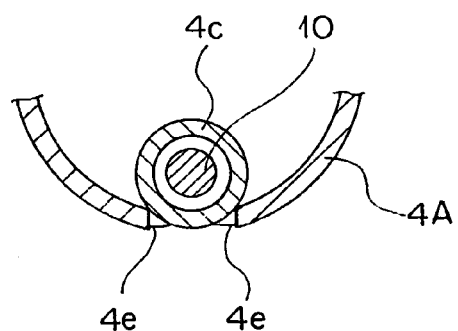
FIG. 29 is a sectional view of a sheath insert section including a holder to be engaged with a wiper shaft.

As shown in FIG. 29, a plurality of holders 4c are arranged in the wiper insert section 4A. For example, two cutouts, one at the distal end and the other at the proximal end of the wiper insert section 4A, are made, and then two holders 4b are respectively laser welded in the two cutouts.

As shown in FIG. 25, the insert section 2A of the rigid endoscope 2 is inserted through the wiper sheath 4. The insertion position of the insert section 2A of the rigid endoscope 2 is determined by the guide portion 5 that is mated with the guide connector 8.

Figure 28:
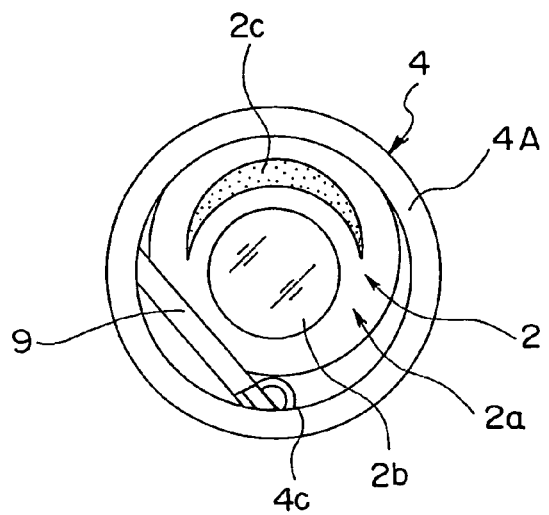
FIG. 28 illustrates the distal-end face of the wiper sheath with the rigid endoscope inserted therein viewed from the distal-end side.

As shown in FIGS. 25 and 28, the distal-end face 2a of the rigid endoscope 2 includes an illumination window 2c aligned with a distal-end face of a light-guide fiber as the illumination optical system, and an observation window 2b forming the most distal end of the observation optical system including an image pickup device such as a charge-coupled device (CCD).

With the insert section 2A of the rigid endoscope 2 inserted to the insertion position within the wiper sheath 4, the illumination window 2c and the observation window 2b have a positional relationship as shown in FIG. 25.

Whereas, the wiper sheath 4 has the rounded end portion 4d. So, if illumination light is emitted from the illumination window 2c as represented by a broken line, the illumination light is reflected from the inner circumference of the rounded end portion 4d, and then incident on the observation window 2b. An observation image may be destroyed.

In accordance with this embodiment, a light-entrance prevention member 30 is arranged on the inner circumference of the rounded end portion 4d of the wiper sheath 4 in order to prevent the reflected light from entering the observation window 2b. The light-entrance prevention member 30 may be one that guides the reflected light to another area rather than the observation window so that an observation image is free from the effect of the reflected light.

Figure 26:
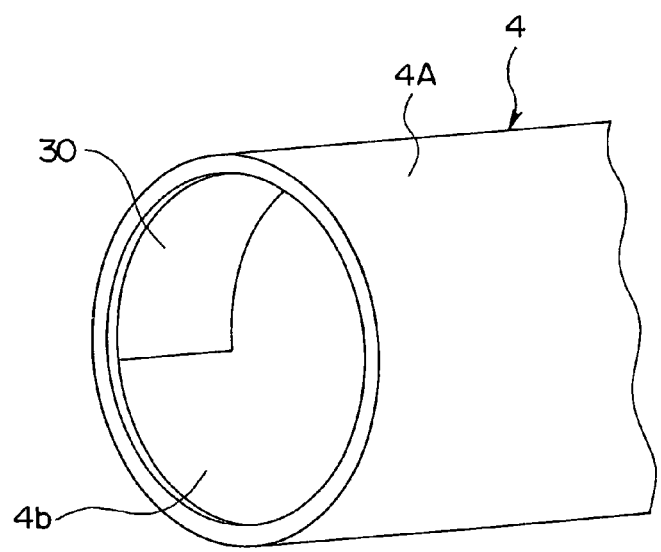
FIG. 26 is a perspective view illustrating the end portion of the wiper sheath with a light-entrance prevention member attached thereto.
Figure 27:
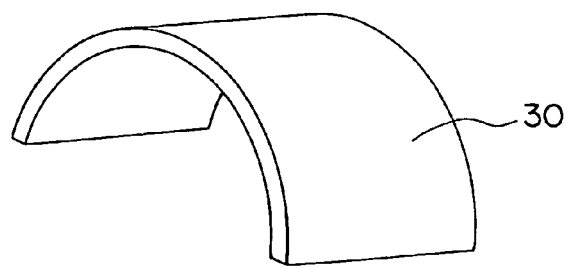
FIG. 27 is a perspective view of the light-entrance prevention member.

As shown in FIG. 27, the light-entrance prevention member 30 may have reflective characteristics, and may be curved to adhere to the inner circumference of the rounded end portion 4d. As shown in FIG. 26, the light-entrance prevention member 30 may adhere to the inner circumference of the rounded end portion 4d of the light-entrance prevention member 30. In this arrangement, a recess portion reflecting the illumination light is eliminated as shown in FIG. 25, and the illumination light that is emitted from the illumination window 2c as represented by broken line is reflected from the light-entrance prevention member 30 as represented by solid line. This arrangement prevents the reflected light from being incident on the observation window 2b and an excellent observation image thus results. More specifically, the thickness of the light-entrance prevention member 30 is determined taking into consideration the projection of the rounded end portion 4d from the inner circumference.

Figure 30:
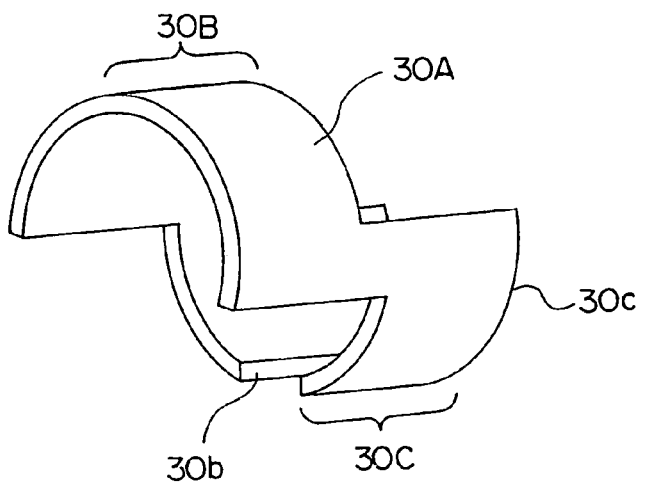
FIG. 30 is a perspective view illustrating a modified example of the light-entrance prevention member.

The light-entrance prevention member 30 may be a light-entrance prevention member 30A of FIG. 30. The light-entrance prevention member 30A includes an anti-reflection portion 30B having anti-reflection characteristics and a position restraining portion 30C. The position restraining portion 30C integrally extends from the proximal end of the light-entrance prevention member 30B and has a cutout 30b on the underside thereof. The holder 4b is arranged within the cutout 30b. That is, the light-entrance prevention member 30A may thus be used to position the wiper shaft 10.

The light-entrance prevention member 30 may be arranged so that the rounded end portion 4d is moved to the distal-end face 2a of the rigid endoscope 2.

The endoscope system 1A does not employ the washing sheath 3. Alternatively, the same advantages are provided even if the endoscope system 1A employs the washing sheath 3.

With the this arrangement, an excellent observation image is obtained while the ease of insertion of the wiper sheath 4 is maintained in the same way as in the previous embodiment.

When the insert section 2A of the rigid endoscope 2 is inserted through the wiper insert section 4A of the wiper sheath 4 in the endoscope system 1A, a gap occurs between the inner circumference of the wiper insert section 4A and the outer circumference of the insert section 2A because the wiper shaft 10 is arranged within the wiper insert section 4A. In this case, the insert section 2A of the rigid endoscope 2 may be loose due to the gap. Then, when the wiper 9 is operated, the distal-end face 2a of the rigid endoscope 2 becomes rattled, and the wiper 9 cannot reliably wipe the distal-end face 2a because the wiper 9 cannot reliably move being in contact with the distal-end face 2a.

Such a problem is overcome by introducing an endoscope system 1B.

The endoscope system 1B is described below with reference to FIGS. 31 through 33.

Figure 31:
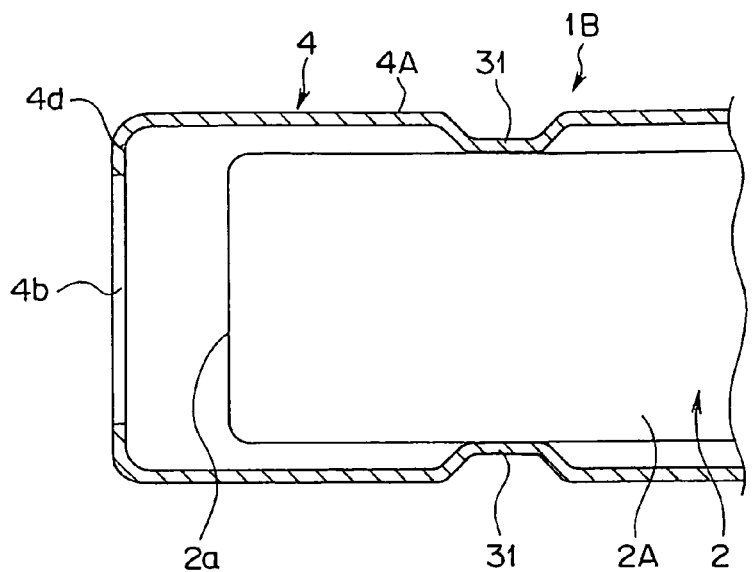
FIG. 31 is a sectional view illustrating another example of the end portion of the wiper sheath forming the endoscope system.

As shown in FIG. 31, a portion of the inner circumference of the distal end of wiper insert section 4A of the wiper sheath 4 forming the endoscope system 1B is inwardly projected toward the center axis of the wiper sheath 4 as a position restraining projection 31. The position restraining projection 31 extends entirely around the circumference of the wiper insert section 4A at a predetermined location.

Figure 32:
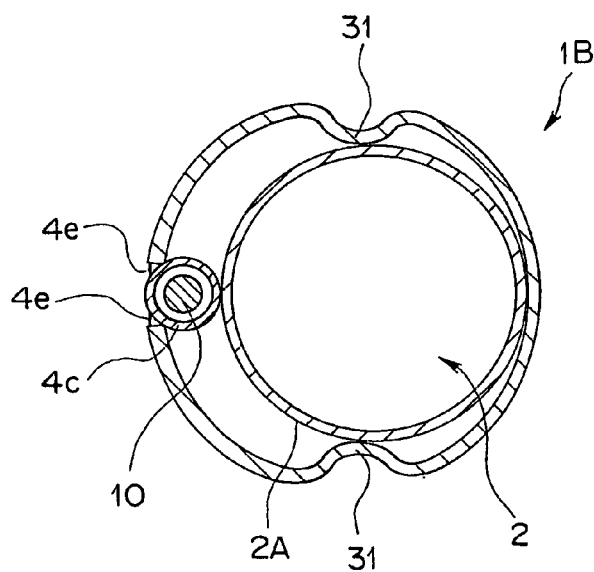
FIG. 32 is a sectional view illustrating the relationship between the end portion of the wiper sheath and the insert section of the rigid endoscope.

Therefore, when the insert section 2A of the rigid endoscope 2 is inserted through the wiper insert section 4A of the wiper sheath 4, the outer circumference of the insert section 2A of the rigid endoscope 2 is brought into contact with the position restraining projection 31 as shown in FIG. 32. The insert section 2A is thus held within the wiper insert section 4A in a manner free from rattling. In this case, as shown in FIG. 32, the outer circumference of the insert section 2A is also brought into contact with the holder 4b provided in the wiper insert section 4A, thereby holding the insert section 2A in a more reliably manner.

The position restraining projection 31 may be arranged in a predetermined location along the axial direction of the wiper insert section 4A (for example, in the center portion of the wiper insert section 4A), or at a plurality of locations within the wiper insert section 4A.

Figure 33:
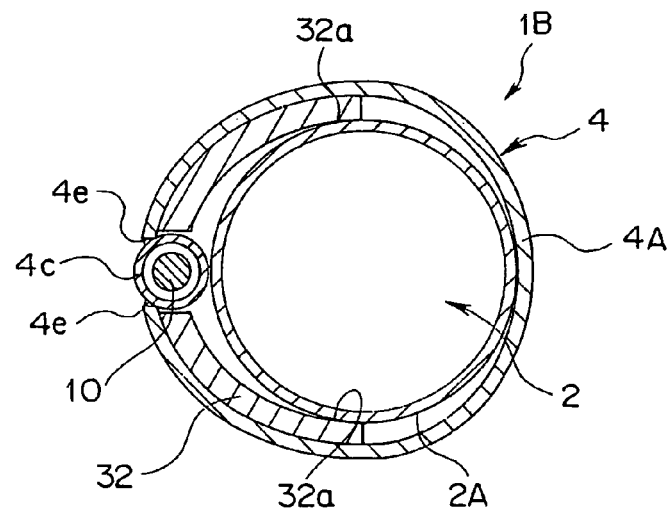
FIG. 33 is a sectional view of yet another example of the end portion of the wiper sheath forming the endoscope system.

As shown in FIG. 33, the position restraining projection may be the light-entrance prevention member 30A discussed with reference to FIG. 30. In this case, the light-entrance prevention member 30A is thickened by a predetermined thickness. In this arrangement, restraining portions 32a having the same effect as the position restraining projection 31 results on both the distal end and the proximal end of the wiper insert section 4A. When inserted through the wiper insert section 4A, the insert section 2A is reliably held within the wiper insert section 4A.

The endoscope system 1B employs no washing sheath 3. The same advantages are provided even if the endoscope system 1B employs the washing sheath 3.

In accordance with the present embodiment, an endoscope system having a simple-structured, low-cost, and easy-to-use wiper is thus provided.

In the above-described embodiments, the shapes of the first cam groove 24 and the second cam groove 25 are not limited to those described with reference to FIG. 10. The first cam groove 24 and the second cam groove 25 may have any shape as long as the wiper 9 is reliably kept apart from the nozzle 3b of the washing sheath 3 and moves along the distal-end face 2a while in contact with the distal-end face 2a.

Have described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system comprising:
    a rigid endoscope including an observation optical system and an illumination optical system in a rigid insert section thereof; and
    a wiper sheath, the wiper sheath including a wiper insert section receiving the insert section of the rigid endoscope, a wiper arranged on a distal end of the wiper insert section and enabled to be placed in contact with a distal-end face of the rigid endoscope received in the wiper insert section, and an operation unit, arranged at a proximal end portion of the wiper insert section, for switching the wiper between a contact state with the wiper placed to be in contact with the distal-end face of the rigid endoscope and a detached state with the wiper spaced apart from the distal-end face of the rigid endoscope, and for moving the wiper on and along the distal-end face of the rigid endoscope when the wiper is in the contact state;
    wherein the operation unit comprises:
    a tubular body secured to the outer circumference of the wiper insert section and having a first cam groove with which a pin is engaged;
    a wiper tube rotatably and longitudinally movably supported around the outer circumference of the tubular body and having one end portion on which the pin to be engaged with the first cam groove is attached;
    a first rotary ring rotatably supported around the outer circumference of the tubular body and forming an outer housing of the operation unit; and
    a second rotary ring with an extension portion having a second cam groove with which the other end portion of the pin attached to the wiper tube is engaged, the second rotary ring rotatably supported around the outer circumference of the tubular body, and integrally formed with the first rotary ring.

2. The endoscope system according to claim 1, further comprising
    a washing sheath including a sheath insert section having an insert channel receiving the insert section of the rigid endoscope, and a nozzle provided at an end portion of the sheath insert section, for supplying a fluid to or sucking a fluid from the distal-end face of the insert section arranged in the insert channel.

3. The endoscope system according to claim 2,
    wherein the operation unit further comprises a pair of O-ring holders for holding an O-ring that is tightly placed on the outer circumference of the insert section of the rigid endoscope inserted in the inner passage of the wiper insert section.

4. The endoscope system according to claim 1, wherein the wiper forming the wiper sheath is connected to one end of a wiper shaft extending through an inner passage of the wiper insert section, and wherein the other end of the wiper shaft is arranged in the operation unit.

5. The endoscope system according to claim 4, wherein the wiper shaft is supported rotatably and axially movably by a holder rigidly secured within the inner passage of the wiper insert section.

6. The endoscope system according to claim 1, wherein the end face of the wiper tube comprises a groove receiving the other end of a wiper shaft having the one end to which the wiper forming the wiper sheath is connected.

7. The endoscope system according to claim 1, wherein the operation unit further comprises a water-tight sheet ring member for assuring water-tightness of the operation unit.

8. The endoscope system according to claim 1, wherein the first cam groove is crank-shaped, and wherein the second cam groove is V-shaped.

* * * * *